United States Patent
Kuo

(10) Patent No.: US 11,026,831 B2
(45) Date of Patent: Jun. 8, 2021

(54) DENTAL APPLIANCE FEATURES FOR SPEECH ENHANCEMENT

(71) Applicant: Align Technology, Inc., San Jose, CA (US)

(72) Inventor: Eric Kuo, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 418 days.

(21) Appl. No.: 15/829,504

(22) Filed: Dec. 1, 2017

(65) Prior Publication Data

US 2018/0153733 A1    Jun. 7, 2018

Related U.S. Application Data

(60) Provisional application No. 62/429,548, filed on Dec. 2, 2016.

(51) Int. Cl.
*A61F 5/58* (2006.01)
*A61C 7/08* (2006.01)

(52) U.S. Cl.
CPC . *A61F 5/58* (2013.01); *A61C 7/08* (2013.01)

(58) Field of Classification Search
CPC .................................. A61C 7/08; A61F 5/58
USPC ....................................................... 600/23–24
See application file for complete search history.

(56) References Cited

U.S. PATENT DOCUMENTS

| | | | |
|---|---|---|---|
| 2,098,867 A * | 11/1937 | Glisson | A61F 5/58 600/24 |
| 2,171,695 A | 9/1939 | Harper | |
| 2,194,790 A | 3/1940 | Gluck | |
| 2,467,432 A | 4/1949 | Kesling | |
| 2,531,222 A | 11/1950 | Kesling | |
| 2,818,065 A * | 12/1957 | Freed | A61F 5/58 600/24 |
| 3,089,487 A | 5/1963 | Enicks et al. | |
| 3,092,907 A | 6/1963 | Traiger | |
| 3,178,820 A | 4/1965 | Kesling | |
| 3,211,143 A | 10/1965 | Grossberg | |
| 3,277,892 A * | 10/1966 | Tepper | A61F 5/00 607/58 |

(Continued)

FOREIGN PATENT DOCUMENTS

| | | |
|---|---|---|
| AU | 517102 B | 11/1977 |
| AU | 3031677 A | 11/1977 |

(Continued)

OTHER PUBLICATIONS

US 8,553,966 B1, 10/2013, Alpern et al. (withdrawn)

(Continued)

*Primary Examiner* — Navin Natnithithadha
*Assistant Examiner* — Sunita Reddy
(74) *Attorney, Agent, or Firm* — Shay Glenn LLP

(57) ABSTRACT

Provided herein are orthodontic devices and methods for patients whose orthodontic devices are causing a lisp. The device can comprise an aligner configured to fit over a patient's dental arch and comprising an occlusal surface section positioned over an occlusal surface of the patient's teeth. The aligner can comprise a barrier portion extending laterally and adjacent to a region of the dental arch, the barrier portion allowing the patient's tongue to form a seal against the barrier portion when the patient is speaking while wearing the device.

17 Claims, 23 Drawing Sheets

(56) References Cited

U.S. PATENT DOCUMENTS

| | | |
|---|---|---|
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,724,075 A | 4/1973 | Kesling |
| 3,738,005 A | 6/1973 | Cohen et al. |
| 3,797,115 A | 3/1974 | Silverman et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,949,477 A | 4/1976 | Cohen et al. |
| 3,950,851 A | 4/1976 | Bergersen |
| 3,955,282 A | 5/1976 | McNall |
| 3,983,628 A | 10/1976 | Acevedo |
| 4,014,096 A | 3/1977 | Dellinger |
| 4,055,895 A | 11/1977 | Huge |
| 4,094,068 A | 6/1978 | Schinhammer |
| 4,117,596 A | 10/1978 | Wallshein |
| 4,129,946 A | 12/1978 | Kennedy |
| 4,134,208 A | 1/1979 | Pearlman |
| 4,139,944 A | 2/1979 | Bergersen |
| 4,179,811 A | 12/1979 | Hinz |
| 4,179,812 A | 12/1979 | White |
| 4,183,141 A | 1/1980 | Dellinger |
| 4,195,046 A | 3/1980 | Kesling |
| 4,204,325 A | 5/1980 | Kaelble |
| 4,253,828 A | 3/1981 | Coles et al. |
| 4,255,138 A | 3/1981 | Frohn |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,368,040 A | 1/1983 | Weissman |
| 4,419,992 A | 12/1983 | Chorbajian |
| 4,433,956 A | 2/1984 | Witzig |
| 4,433,960 A | 2/1984 | Garito et al. |
| 4,439,154 A | 3/1984 | Mayclin |
| 4,449,928 A | 5/1984 | von Weissenfluh |
| 4,478,580 A | 10/1984 | Barrut |
| 4,500,294 A | 2/1985 | Lewis |
| 4,505,672 A | 3/1985 | Kurz |
| 4,505,673 A | 3/1985 | Yoshii |
| 4,519,386 A | 5/1985 | Sullivan |
| 4,523,908 A | 6/1985 | Drisaldi et al. |
| 4,526,540 A | 7/1985 | Dellinger |
| 4,553,936 A | 11/1985 | Wang |
| 4,575,330 A | 3/1986 | Hull |
| 4,575,805 A | 3/1986 | Moermann et al. |
| 4,591,341 A | 5/1986 | Andrews |
| 4,608,021 A | 8/1986 | Barrett |
| 4,609,349 A | 9/1986 | Cain |
| 4,611,288 A | 9/1986 | Duret et al. |
| 4,629,424 A | 12/1986 | Lauks et al. |
| 4,638,145 A | 1/1987 | Sakuma et al. |
| 4,656,860 A | 4/1987 | Orthuber et al. |
| 4,663,720 A | 5/1987 | Duret et al. |
| 4,664,626 A | 5/1987 | Kesling |
| 4,665,621 A | 5/1987 | Ackerman et al. |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,790,752 A | 12/1988 | Cheslak |
| 4,793,803 A | 12/1988 | Martz |
| 4,798,534 A | 1/1989 | Breads |
| 4,830,612 A | 5/1989 | Bergersen |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,901,737 A | 2/1990 | Toone |
| 4,932,866 A | 6/1990 | Guis |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,971,557 A | 11/1990 | Martin |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,015,183 A | 5/1991 | Fenick |
| 5,017,133 A | 5/1991 | Miura |
| 5,018,969 A | 5/1991 | Andreiko et al. |
| 5,027,281 A | 6/1991 | Rekow et al. |
| 5,035,613 A | 7/1991 | Breads et al. |
| 5,037,295 A | 8/1991 | Bergersen |
| 5,055,039 A | 10/1991 | Abbatte et al. |
| 5,061,839 A | 10/1991 | Matsuno et al. |
| 5,083,919 A | 1/1992 | Quachi |
| 5,094,614 A | 3/1992 | Wildman |
| 5,100,316 A | 3/1992 | Wildman |
| 5,103,838 A | 4/1992 | Yousif |
| 5,114,339 A | 5/1992 | Guis |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,194,003 A | 3/1993 | Garay et al. |
| 5,204,670 A | 4/1993 | Stinton |
| 5,222,499 A | 6/1993 | Allen et al. |
| 5,224,049 A | 6/1993 | Mushabac |
| 5,238,404 A | 8/1993 | Andreiko |
| 5,242,304 A | 9/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,312,247 A | 5/1994 | Sachdeva et al. |
| 5,314,335 A | 5/1994 | Fung |
| 5,324,186 A | 6/1994 | Bakanowski |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,344,315 A | 9/1994 | Hanson |
| 5,368,478 A | 11/1994 | Andreiko et al. |
| 5,372,502 A | 12/1994 | Massen et al. |
| D354,355 S | 1/1995 | Hilgers |
| 5,382,164 A | 1/1995 | Stern |
| 5,395,238 A | 3/1995 | Andreiko et al. |
| 5,415,542 A | 5/1995 | Kesling |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,449,703 A | 9/1995 | Mitra et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |

(56) References Cited

U.S. PATENT DOCUMENTS

| | | |
|---|---|---|
| 5,487,662 A | 1/1996 | Kipke et al. |
| RE35,169 E | 3/1996 | Lemchen et al. |
| 5,499,633 A | 3/1996 | Fenton |
| 5,522,725 A | 6/1996 | Jordan et al. |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,575,655 A | 11/1996 | Darnell |
| 5,583,977 A | 12/1996 | Seidl |
| 5,587,912 A | 12/1996 | Andersson et al. |
| 5,588,098 A | 12/1996 | Chen et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,636,736 A | 6/1997 | Jacobs et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,711,665 A | 1/1998 | Adam et al. |
| 5,711,666 A | 1/1998 | Hanson |
| 5,725,376 A | 3/1998 | Poirier |
| 5,725,378 A | 3/1998 | Wang |
| 5,730,151 A | 3/1998 | Summer et al. |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,162 A | 9/1998 | Shimodaira et al. |
| 5,800,174 A | 9/1998 | Andersson |
| 5,813,854 A | 9/1998 | Nikodem |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,876,199 A | 3/1999 | Bergersen |
| 5,879,158 A | 3/1999 | Doyle et al. |
| 5,880,961 A | 3/1999 | Crump |
| 5,880,962 A | 3/1999 | Andersson et al. |
| 5,882,192 A | 3/1999 | Bergersen |
| 5,886,702 A | 3/1999 | Migdal et al. |
| 5,890,896 A | 4/1999 | Padial |
| 5,904,479 A | 5/1999 | Staples |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,975,906 A | 11/1999 | Knutson |
| 5,980,246 A | 11/1999 | Ramsay et al. |
| 5,989,023 A | 11/1999 | Summer et al. |
| 6,002,706 A | 12/1999 | Staver et al. |
| 6,018,713 A | 1/2000 | Coli et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,070,140 A | 5/2000 | Tran |
| 6,099,303 A | 8/2000 | Gibbs et al. |
| 6,099,314 A | 8/2000 | Kopelman et al. |
| 6,102,701 A | 8/2000 | Engeron |
| 6,120,287 A | 9/2000 | Chen |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,183,249 B1 | 2/2001 | Brennan et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,210,162 B1 | 4/2001 | Chishti et al. |
| 6,212,435 B1 | 4/2001 | Lattner et al. |
| 6,213,767 B1 | 4/2001 | Dixon et al. |
| 6,217,334 B1 | 4/2001 | Hultgren |
| 6,227,850 B1 | 5/2001 | Chishti et al. |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,283,761 B1 | 9/2001 | Joao |
| 6,288,138 B1 | 9/2001 | Yamamoto |
| 6,299,438 B1 | 10/2001 | Sahagian et al. |
| 6,309,215 B1 | 10/2001 | Phan et al. |
| 6,313,432 B1 | 11/2001 | Nagata et al. |
| 6,315,553 B1 | 11/2001 | Sachdeva et al. |
| 6,328,745 B1 | 12/2001 | Ascherman |
| 6,332,774 B1 | 12/2001 | Chikami |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,386,878 B1 | 5/2002 | Pavlovskaia et al. |
| 6,394,802 B1 | 5/2002 | Hahn |
| 6,402,510 B1 | 6/2002 | Williams |
| 6,402,707 B1 | 6/2002 | Ernst |
| 6,405,729 B1 | 6/2002 | Thornton |
| 6,406,292 B1 | 6/2002 | Chishti et al. |
| 6,409,504 B1 | 6/2002 | Jones et al. |
| 6,413,086 B1 | 7/2002 | Womack |
| 6,414,264 B1 | 7/2002 | von Falkenhausen |
| 6,414,708 B1 | 7/2002 | Carmeli et al. |
| 6,435,871 B1 | 8/2002 | Inman |
| 6,436,058 B1 | 8/2002 | Krahner et al. |
| 6,441,354 B1 | 8/2002 | Seghatol et al. |
| 6,450,167 B1 | 9/2002 | David et al. |
| 6,450,807 B1 | 9/2002 | Chishti et al. |
| 6,462,301 B1 | 10/2002 | Scott et al. |
| 6,470,338 B1 | 10/2002 | Rizzo et al. |
| 6,471,511 B1 | 10/2002 | Chishti et al. |
| 6,471,512 B1 | 10/2002 | Sachdeva et al. |
| 6,471,970 B1 | 10/2002 | Fanara et al. |
| 6,482,002 B2 | 11/2002 | Jordan et al. |
| 6,482,298 B1 | 11/2002 | Bhatnagar |
| 6,496,814 B1 | 12/2002 | Busche |
| 6,496,816 B1 | 12/2002 | Thiesson et al. |
| 6,499,026 B1 | 12/2002 | Rivette et al. |
| 6,499,995 B1 | 12/2002 | Schwartz |
| 6,507,832 B1 | 1/2003 | Evans et al. |
| 6,514,074 B1 | 2/2003 | Chishti et al. |
| 6,515,593 B1 | 2/2003 | Stark et al. |
| 6,516,288 B2 | 2/2003 | Bagne |
| 6,516,805 B1 | 2/2003 | Thornton |
| 6,520,772 B2 | 2/2003 | Williams |
| 6,523,009 B1 | 2/2003 | Wilkins |
| 6,523,019 B1 | 2/2003 | Borthwick |
| 6,524,101 B1 | 2/2003 | Phan et al. |
| 6,526,168 B1 | 2/2003 | Ornes et al. |
| 6,526,982 B1 | 3/2003 | Strong |
| 6,529,891 B1 | 3/2003 | Heckerman |
| 6,529,902 B1 | 3/2003 | Kanevsky et al. |
| 6,532,455 B1 | 3/2003 | Martin et al. |
| 6,535,865 B1 | 3/2003 | Skaaning et al. |
| 6,540,512 B1 | 4/2003 | Sachdeva et al. |
| 6,540,707 B1 | 4/2003 | Stark et al. |
| 6,542,593 B1 | 4/2003 | Bowman Amuah |
| 6,542,881 B1 | 4/2003 | Meidan et al. |

(56) References Cited

U.S. PATENT DOCUMENTS

| | | |
|---|---|---|
| 6,542,894 B1 | 4/2003 | Lee et al. |
| 6,542,903 B2 | 4/2003 | Hull et al. |
| 6,551,243 B2 | 4/2003 | Bocionek et al. |
| 6,554,837 B1 | 4/2003 | Hauri et al. |
| 6,556,659 B1 | 4/2003 | Bowman Amuah |
| 6,556,977 B1 | 4/2003 | Lapointe et al. |
| 6,560,592 B1 | 5/2003 | Reid et al. |
| 6,564,209 B1 | 5/2003 | Dempski et al. |
| 6,567,814 B1 | 5/2003 | Bankier et al. |
| 6,571,227 B1 | 5/2003 | Agrafiotis et al. |
| 6,572,372 B1 | 6/2003 | Phan et al. |
| 6,573,998 B2 | 6/2003 | Cohen Sabban |
| 6,574,561 B2 | 6/2003 | Alexander et al. |
| 6,578,003 B1 | 6/2003 | Camarda et al. |
| 6,580,948 B2 | 6/2003 | Haupert et al. |
| 6,587,529 B1 | 7/2003 | Staszewski et al. |
| 6,587,828 B1 | 7/2003 | Sachdeva |
| 6,592,368 B1 | 7/2003 | Weathers |
| 6,594,539 B1 | 7/2003 | Geng |
| 6,595,342 B1 | 7/2003 | Maritzen et al. |
| 6,597,934 B1 | 7/2003 | de Jong et al. |
| 6,598,043 B1 | 7/2003 | Baclawski |
| 6,599,250 B2 | 7/2003 | Webb et al. |
| 6,602,070 B2 | 8/2003 | Miller et al. |
| 6,604,527 B1 | 8/2003 | Palmisano |
| 6,606,744 B1 | 8/2003 | Mikurak |
| 6,607,382 B1 | 8/2003 | Kuo et al. |
| 6,611,783 B2 | 8/2003 | Kelly et al. |
| 6,611,867 B1 | 8/2003 | Bowman Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinbold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,682,346 B2 | 1/2004 | Chishti et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Wang et al. |
| 6,694,234 B2 | 2/2004 | Lockwood et al. |
| 6,697,164 B1 | 2/2004 | Babayoff et al. |
| 6,697,793 B2 | 2/2004 | McGreevy |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,736,638 B1 | 5/2004 | Sachdeva et al. |
| 6,739,869 B1 | 5/2004 | Taub et al. |
| 6,744,932 B1 | 6/2004 | Rubbert et al. |
| 6,749,414 B1 | 6/2004 | Hanson et al. |
| 6,769,913 B2 | 8/2004 | Hurson |
| 6,772,026 B2 | 8/2004 | Bradbury et al. |
| 6,790,036 B2 | 9/2004 | Graham |
| 6,802,713 B1 | 10/2004 | Chishti et al. |
| 6,814,574 B2 | 11/2004 | Abolfathi et al. |
| 6,830,450 B2 | 12/2004 | Knopp et al. |
| 6,832,912 B2 | 12/2004 | Mao |
| 6,832,914 B1 | 12/2004 | Bonnet et al. |
| 6,843,370 B2 | 1/2005 | Tuneberg |
| 6,845,175 B2 | 1/2005 | Kopelman et al. |
| 6,885,464 B1 | 4/2005 | Pfeiffer et al. |
| 6,890,285 B2 | 5/2005 | Rahman et al. |
| 6,951,254 B2 | 10/2005 | Morrison |
| 6,976,841 B1 | 12/2005 | Osterwalder |
| 6,978,268 B2 | 12/2005 | Thomas et al. |
| 6,983,752 B2 | 1/2006 | Garabadian |
| 6,984,128 B2 | 1/2006 | Breining et al. |
| 6,988,893 B2 | 1/2006 | Haywood |
| 7,016,952 B2 | 3/2006 | Mullen et al. |
| 7,020,963 B2 | 4/2006 | Cleary et al. |
| 7,036,514 B2 | 5/2006 | Heck |
| 7,040,896 B2 | 5/2006 | Pavlovskaia et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,156,661 B2 | 1/2007 | Choi et al. |
| 7,166,063 B2 | 1/2007 | Rahman et al. |
| 7,184,150 B2 | 2/2007 | Quadling et al. |
| 7,191,451 B2 | 3/2007 | Nakagawa |
| 7,192,273 B2 | 3/2007 | McSurdy |
| 7,217,131 B2 | 5/2007 | Vuillemot |
| 7,220,122 B2 | 5/2007 | Chishti |
| 7,220,124 B2 | 5/2007 | Taub et al. |
| 7,229,282 B2 | 6/2007 | Andreiko et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,245,753 B2 | 7/2007 | Squilla et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,294,141 B2 | 11/2007 | Bergersen |
| 7,302,842 B2 | 12/2007 | Biester et al. |
| 7,320,592 B2 | 1/2008 | Chishti et al. |
| 7,328,706 B2 | 2/2008 | Barach et al. |
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,354,270 B2 | 4/2008 | Abolfathi et al. |
| 7,357,637 B2 | 4/2008 | Liechtung |
| 7,435,083 B2 | 10/2008 | Chishti et al. |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,543,511 B2 | 6/2009 | Kimura et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,637,740 B2 | 12/2009 | Knopp |
| 7,641,473 B2 | 1/2010 | Sporbert et al. |
| 7,668,355 B2 | 2/2010 | Wong et al. |
| 7,670,179 B2 | 3/2010 | Muller |
| 7,695,327 B2 | 4/2010 | Bäuerle et al. |
| 7,698,068 B2 | 4/2010 | Babayoff |
| 7,711,447 B2 | 5/2010 | Lu et al. |
| 7,724,378 B2 | 5/2010 | Babayoff |
| D618,619 S | 6/2010 | Walter |

(56) References Cited

U.S. PATENT DOCUMENTS

| | | |
|---|---|---|
| 7,728,848 B2 | 6/2010 | Petrov et al. |
| 7,731,508 B2 | 6/2010 | Borst |
| 7,735,217 B2 | 6/2010 | Borst |
| 7,740,476 B2 | 6/2010 | Rubbed et al. |
| 7,744,369 B2 | 6/2010 | Imgrund et al. |
| 7,746,339 B2 | 6/2010 | Matov et al. |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,841,464 B2 | 11/2010 | Cinader et al. |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,869,983 B2 | 1/2011 | Raby et al. |
| 7,872,760 B2 | 1/2011 | Ertl |
| 7,874,836 B2 | 1/2011 | McSurdy |
| 7,874,837 B2 | 1/2011 | Chishti et al. |
| 7,874,849 B2 | 1/2011 | Sticker et al. |
| 7,878,801 B2 | 2/2011 | Abolfathi et al. |
| 7,878,805 B2 | 2/2011 | Moss et al. |
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,929,151 B2 | 4/2011 | Liang et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,970,627 B2 | 6/2011 | Kuo et al. |
| 7,985,414 B2 | 7/2011 | Knaack et al. |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,029,277 B2 | 10/2011 | Imgrund et al. |
| 8,038,444 B2 | 10/2011 | Kitching et al. |
| 8,045,772 B2 | 10/2011 | Kosuge et al. |
| 8,054,556 B2 | 11/2011 | Chen et al. |
| 8,070,490 B1 | 12/2011 | Roetzer et al. |
| 8,075,306 B2 | 12/2011 | Kitching et al. |
| 8,077,949 B2 | 12/2011 | Liang et al. |
| 8,083,556 B2 | 12/2011 | Stadler et al. |
| D652,799 S | 1/2012 | Mueller |
| 8,092,215 B2 | 1/2012 | Stone-Collonge et al. |
| 8,095,383 B2 | 1/2012 | Arnone et al. |
| 8,099,268 B2 | 1/2012 | Kitching et al. |
| 8,099,305 B2 | 1/2012 | Kuo et al. |
| 8,118,592 B2 | 2/2012 | Tortorici |
| 8,126,025 B2 | 2/2012 | Takeda |
| 8,136,529 B2 | 3/2012 | Kelly |
| 8,144,954 B2 | 3/2012 | Quadling et al. |
| 8,160,334 B2 | 4/2012 | Thiel et al. |
| 8,172,569 B2 | 5/2012 | Matty et al. |
| 8,197,252 B1 | 6/2012 | Harrison |
| 8,201,560 B2 | 6/2012 | Dembro |
| 8,215,312 B2 | 7/2012 | Garabadian et al. |
| 8,240,018 B2 | 8/2012 | Walter et al. |
| 8,275,180 B2 | 9/2012 | Kuo |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,401,826 B2 | 3/2013 | Cheng et al. |
| 8,419,428 B2 | 4/2013 | Lawrence |
| 8,433,083 B2 | 4/2013 | Abolfathi et al. |
| 8,439,672 B2 | 5/2013 | Matov et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,517,726 B2 | 8/2013 | Kakavand et al. |
| 8,520,922 B2 | 8/2013 | Wang et al. |
| 8,520,925 B2 | 8/2013 | Duret et al. |
| 8,523,565 B2 | 9/2013 | Matty et al. |
| 8,545,221 B2 | 10/2013 | Stone-Collonge et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,601,925 B1 | 12/2013 | Coto |
| 8,639,477 B2 | 1/2014 | Chelnokov et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,738,394 B2 | 5/2014 | Kuo |
| 8,743,923 B2 | 6/2014 | Geske et al. |
| 8,753,114 B2 | 6/2014 | Vuillemot |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,843,381 B2 | 9/2014 | Kuo et al. |
| 8,856,053 B2 | 10/2014 | Mah |
| 8,870,566 B2 | 10/2014 | Bergersen |
| 8,874,452 B2 | 10/2014 | Kuo |
| 8,878,905 B2 | 11/2014 | Fisker et al. |
| 8,899,976 B2 | 12/2014 | Chen et al. |
| 8,936,463 B2 | 1/2015 | Mason et al. |
| 8,944,812 B2 | 2/2015 | Kou |
| 8,948,482 B2 | 2/2015 | Levin |
| 8,956,058 B2 | 2/2015 | Rosch |
| 8,992,216 B2 | 3/2015 | Karazivan |
| 9,004,915 B2 | 4/2015 | Moss et al. |
| 9,022,792 B2 | 5/2015 | Sticker et al. |
| 9,039,418 B1 | 5/2015 | Rubbed |
| 9,084,535 B2 | 7/2015 | Girkin et al. |
| 9,084,657 B2 | 7/2015 | Matty et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,211,166 B2 | 12/2015 | Kuo et al. |
| 9,214,014 B2 | 12/2015 | Levin |
| 9,220,580 B2 | 12/2015 | Borovinskih et al. |
| 9,241,774 B2 | 1/2016 | Li et al. |
| 9,242,118 B2 | 1/2016 | Brawn |
| 9,261,358 B2 | 2/2016 | Atiya et al. |
| 9,277,972 B2 | 3/2016 | Brandt et al. |
| 9,336,336 B2 | 5/2016 | Deichmann et al. |
| 9,351,810 B2 | 5/2016 | Moon |
| 9,375,300 B2 | 6/2016 | Matov et al. |
| 9,403,238 B2 | 8/2016 | Culp |
| 9,408,743 B1 | 8/2016 | Wagner |
| 9,414,897 B2 | 8/2016 | Wu et al. |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,463,287 B1 | 10/2016 | Lorberbaum et al. |
| 9,492,243 B2 | 11/2016 | Kuo |
| 9,500,635 B2 | 11/2016 | Islam |
| 9,506,808 B2 | 11/2016 | Jeon et al. |
| 9,510,918 B2 | 12/2016 | Sanchez |
| 9,545,331 B2 | 1/2017 | Ingemarsson-Matzen |
| 9,566,132 B2 | 2/2017 | Stone-Collonge et al. |
| 9,584,771 B2 | 2/2017 | Mandelis et al. |
| 9,589,329 B2 | 3/2017 | Levin |
| 9,675,427 B2 | 6/2017 | Kopelman |
| 9,675,430 B2 | 6/2017 | Verker et al. |
| 9,693,839 B2 | 7/2017 | Atiya et al. |
| 9,744,006 B2 | 8/2017 | Ross |

(56) References Cited

U.S. PATENT DOCUMENTS

| | | |
|---|---|---|
| 9,820,829 B2 | 11/2017 | Kuo |
| 9,830,688 B2 | 11/2017 | Levin |
| 9,844,421 B2 | 12/2017 | Moss et al. |
| 9,848,985 B2 | 12/2017 | Yang et al. |
| 9,861,451 B1 | 1/2018 | Davis |
| 9,936,186 B2 | 4/2018 | Jesenko et al. |
| 10,123,853 B2 | 11/2018 | Moss et al. |
| 10,159,541 B2 | 12/2018 | Bindayel |
| 10,172,693 B2 | 1/2019 | Brandt et al. |
| 10,195,690 B2 | 2/2019 | Culp |
| 10,231,801 B2 | 3/2019 | Korytov et al. |
| 10,238,472 B2 | 3/2019 | Levin |
| 10,258,432 B2 | 4/2019 | Webber |
| 2001/0002310 A1 | 5/2001 | Chishti et al. |
| 2001/0032100 A1 | 10/2001 | Mahmud et al. |
| 2001/0038705 A1 | 11/2001 | Rubbert et al. |
| 2001/0041320 A1 | 11/2001 | Phan et al. |
| 2002/0004727 A1 | 1/2002 | Knaus et al. |
| 2002/0007284 A1 | 1/2002 | Schurenberg et al. |
| 2002/0010568 A1 | 1/2002 | Rubbert et al. |
| 2002/0015934 A1 | 2/2002 | Rubbert et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0035572 A1 | 3/2002 | Takatori et al. |
| 2002/0064752 A1 | 5/2002 | Durbin et al. |
| 2002/0064759 A1 | 5/2002 | Durbin et al. |
| 2002/0087551 A1 | 7/2002 | Hickey et al. |
| 2002/0107853 A1 | 8/2002 | Hofmann et al. |
| 2002/0188478 A1 | 12/2002 | Breeland et al. |
| 2002/0192617 A1 | 12/2002 | Phan et al. |
| 2003/0000927 A1 | 1/2003 | Kanaya et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0049581 A1 | 3/2003 | Deluke |
| 2003/0057192 A1 | 3/2003 | Patel |
| 2003/0059736 A1 | 3/2003 | Lai et al. |
| 2003/0060532 A1 | 3/2003 | Subelka et al. |
| 2003/0068598 A1 | 4/2003 | Vallittu et al. |
| 2003/0095697 A1 | 5/2003 | Wood et al. |
| 2003/0101079 A1 | 5/2003 | McLaughlin |
| 2003/0103060 A1 | 6/2003 | Anderson et al. |
| 2003/0120517 A1 | 6/2003 | Eida et al. |
| 2003/0139834 A1 | 7/2003 | Nikolskiy et al. |
| 2003/0144886 A1 | 7/2003 | Taira |
| 2003/0172043 A1 | 9/2003 | Guyon et al. |
| 2003/0190575 A1 | 10/2003 | Hilliard |
| 2003/0192867 A1 | 10/2003 | Yamazaki et al. |
| 2003/0207224 A1 | 11/2003 | Lotte |
| 2003/0215764 A1 | 11/2003 | Kopelman et al. |
| 2003/0224311 A1 | 12/2003 | Cronauer |
| 2003/0224313 A1 | 12/2003 | Bergersen |
| 2003/0224314 A1 | 12/2003 | Bergersen |
| 2004/0002873 A1 | 1/2004 | Sachdeva |
| 2004/0009449 A1 | 1/2004 | Mah et al. |
| 2004/0013994 A1 | 1/2004 | Goldberg et al. |
| 2004/0019262 A1 | 1/2004 | Perelgut |
| 2004/0029078 A1 | 2/2004 | Marshall |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |
| 2004/0068199 A1 | 4/2004 | Echauz et al. |
| 2004/0078222 A1 | 4/2004 | Khan et al. |
| 2004/0080621 A1 | 4/2004 | Fisher et al. |
| 2004/0094165 A1 | 5/2004 | Cook |
| 2004/0107118 A1 | 6/2004 | Harnsberger et al. |
| 2004/0133083 A1 | 7/2004 | Comaniciu et al. |
| 2004/0152036 A1 | 8/2004 | Abolfathi |
| 2004/0158194 A1 | 8/2004 | Wolff et al. |
| 2004/0166463 A1 | 8/2004 | Wen et al. |
| 2004/0167646 A1 | 8/2004 | Jelonek et al. |
| 2004/0170941 A1 | 9/2004 | Phan et al. |
| 2004/0193036 A1 | 9/2004 | Zhou et al. |
| 2004/0197728 A1 | 10/2004 | Abolfathi et al. |
| 2004/0214128 A1 | 10/2004 | Sachdeva et al. |
| 2004/0219479 A1 | 11/2004 | Malin et al. |
| 2004/0220691 A1 | 11/2004 | Hofmeister et al. |
| 2004/0229185 A1 | 11/2004 | Knopp |
| 2004/0259049 A1 | 12/2004 | Kopelman et al. |
| 2005/0003318 A1 | 1/2005 | Choi et al. |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0038669 A1 | 2/2005 | Sachdeva et al. |
| 2005/0040551 A1 | 2/2005 | Biegler et al. |
| 2005/0042569 A1 | 2/2005 | Plan et al. |
| 2005/0042577 A1 | 2/2005 | Kvitrud et al. |
| 2005/0048433 A1 | 3/2005 | Hilliard |
| 2005/0074717 A1 | 4/2005 | Cleary et al. |
| 2005/0089822 A1 | 4/2005 | Geng |
| 2005/0100333 A1 | 5/2005 | Kerschbaumer et al. |
| 2005/0108052 A1 | 5/2005 | Omaboe |
| 2005/0131738 A1 | 6/2005 | Morris |
| 2005/0144150 A1 | 6/2005 | Ramamurthy et al. |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0216314 A1 | 9/2005 | Secor |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0244791 A1 | 11/2005 | Davis et al. |
| 2005/0271996 A1 | 12/2005 | Sporbert et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0093982 A1 | 5/2006 | Wen |
| 2006/0098007 A1 | 5/2006 | Rouet et al. |
| 2006/0099545 A1 | 5/2006 | Lia et al. |
| 2006/0099546 A1 | 5/2006 | Bergersen |
| 2006/0110698 A1 | 5/2006 | Robson |
| 2006/0111631 A1 | 5/2006 | Kelliher et al. |
| 2006/0115785 A1 | 6/2006 | Li et al. |
| 2006/0137813 A1 | 6/2006 | Robrecht et al. |
| 2006/0147872 A1 | 7/2006 | Andreiko |
| 2006/0154198 A1 | 7/2006 | Durbin et al. |
| 2006/0154207 A1 | 7/2006 | Kuo |
| 2006/0173715 A1 | 8/2006 | Wang |
| 2006/0183082 A1 | 8/2006 | Quadling et al. |
| 2006/0188834 A1 | 8/2006 | Hilliard |
| 2006/0188848 A1 | 8/2006 | Tricca et al. |
| 2006/0194163 A1 | 8/2006 | Tricca et al. |
| 2006/0199153 A1 | 9/2006 | Liu et al. |
| 2006/0204078 A1 | 9/2006 | Orth et al. |
| 2006/0223022 A1 | 10/2006 | Solomon |
| 2006/0223023 A1 | 10/2006 | Lai et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1 | 11/2006 | De Dominicis |
| 2006/0275729 A1 | 12/2006 | Fornoff |
| 2006/0275731 A1 | 12/2006 | Wen et al. |
| 2006/0275736 A1 | 12/2006 | Wen et al. |
| 2006/0277075 A1 | 12/2006 | Salwan |
| 2006/0290693 A1 | 12/2006 | Zhou et al. |
| 2006/0292520 A1 | 12/2006 | Dillon et al. |
| 2007/0031775 A1 | 2/2007 | Andreiko |
| 2007/0037111 A1 | 2/2007 | Mailyn |
| 2007/0037112 A1 | 2/2007 | Mailyn |
| 2007/0046865 A1 | 3/2007 | Umeda et al. |
| 2007/0053048 A1 | 3/2007 | Kumar et al. |
| 2007/0054237 A1 | 3/2007 | Neuschafer |
| 2007/0065768 A1 | 3/2007 | Nadav |
| 2007/0087300 A1 | 4/2007 | Willison et al. |
| 2007/0087302 A1 | 4/2007 | Reising et al. |
| 2007/0106138 A1 | 5/2007 | Beiski et al. |
| 2007/0122592 A1 | 5/2007 | Anderson et al. |

(56) References Cited

U.S. PATENT DOCUMENTS

| | | |
|---|---|---|
| 2007/0128574 A1 | 6/2007 | Kuo et al. |
| 2007/0141525 A1 | 6/2007 | Cinader, Jr. |
| 2007/0141526 A1 | 6/2007 | Eisenberg et al. |
| 2007/0143135 A1 | 6/2007 | Lindquist et al. |
| 2007/0168152 A1 | 7/2007 | Matov et al. |
| 2007/0172112 A1 | 7/2007 | Paley et al. |
| 2007/0172291 A1 | 7/2007 | Yokoyama |
| 2007/0178420 A1 | 8/2007 | Keski-Nisula et al. |
| 2007/0183633 A1 | 8/2007 | Hoffmann |
| 2007/0184402 A1 | 8/2007 | Boutoussov et al. |
| 2007/0185732 A1 | 8/2007 | Hicks et al. |
| 2007/0192137 A1 | 8/2007 | Ombrellaro |
| 2007/0199929 A1 | 8/2007 | Rippl et al. |
| 2007/0215582 A1 | 9/2007 | Roeper et al. |
| 2007/0218422 A1 | 9/2007 | Ehrenfeld |
| 2007/0231765 A1 | 10/2007 | Phan et al. |
| 2007/0238065 A1 | 10/2007 | Sherwood et al. |
| 2007/0239488 A1 | 10/2007 | DeRosso |
| 2007/0263226 A1 | 11/2007 | Kurtz et al. |
| 2008/0013727 A1 | 1/2008 | Uemura |
| 2008/0020350 A1 | 1/2008 | Matov et al. |
| 2008/0045053 A1 | 2/2008 | Stadler et al. |
| 2008/0057461 A1 | 3/2008 | Cheng et al. |
| 2008/0057467 A1 | 3/2008 | Gittelson |
| 2008/0057479 A1 | 3/2008 | Grenness |
| 2008/0059238 A1 | 3/2008 | Park et al. |
| 2008/0090208 A1 | 4/2008 | Rubbert |
| 2008/0094389 A1 | 4/2008 | Rouet et al. |
| 2008/0113317 A1 | 5/2008 | Kemp et al. |
| 2008/0115791 A1 | 5/2008 | Heine |
| 2008/0118882 A1 | 5/2008 | Su |
| 2008/0118886 A1 | 5/2008 | Liang et al. |
| 2008/0141534 A1 | 6/2008 | Hilliard |
| 2008/0171934 A1 | 7/2008 | Greenan et al. |
| 2008/0176448 A1 | 7/2008 | Muller et al. |
| 2008/0233530 A1 | 9/2008 | Cinader |
| 2008/0242144 A1 | 10/2008 | Dietz |
| 2008/0248443 A1 | 10/2008 | Chishti et al. |
| 2008/0254402 A1 | 10/2008 | Hilliard |
| 2008/0254403 A1 | 10/2008 | Hilliard |
| 2008/0268400 A1 | 10/2008 | Moss et al. |
| 2008/0306724 A1 | 12/2008 | Kitching et al. |
| 2009/0029310 A1 | 1/2009 | Pumphrey et al. |
| 2009/0030290 A1 | 1/2009 | Kozuch et al. |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kaneko et al. |
| 2009/0087050 A1 | 4/2009 | Gandyra |
| 2009/0098502 A1 | 4/2009 | Andreiko |
| 2009/0099445 A1 | 4/2009 | Burger |
| 2009/0103579 A1 | 4/2009 | Ushimaru et al. |
| 2009/0105523 A1 | 4/2009 | Kassayan et al. |
| 2009/0130620 A1 | 5/2009 | Yazdi et al. |
| 2009/0136890 A1 | 5/2009 | Kang et al. |
| 2009/0136893 A1 | 5/2009 | Zegarelli |
| 2009/0148809 A1 | 6/2009 | Kuo et al. |
| 2009/0170050 A1 | 7/2009 | Marcus |
| 2009/0181346 A1 | 7/2009 | Orth |
| 2009/0191502 A1 | 7/2009 | Cao et al. |
| 2009/0210032 A1 | 8/2009 | Beiski et al. |
| 2009/0218514 A1 | 9/2009 | Klunder et al. |
| 2009/0246726 A1 | 10/2009 | Chelnokov et al. |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0305540 A1 | 12/2009 | Stadler et al. |
| 2009/0316966 A1 | 12/2009 | Marshall et al. |
| 2009/0317757 A1 | 12/2009 | Lemchen |
| 2010/0015565 A1 | 1/2010 | Carrillo Gonzalez et al. |
| 2010/0019170 A1 | 1/2010 | Hart et al. |
| 2010/0028825 A1 | 2/2010 | Lemchen |
| 2010/0045902 A1 | 2/2010 | Ikeda et al. |
| 2010/0047732 A1 | 2/2010 | Park |
| 2010/0062394 A1 | 3/2010 | Jones et al. |
| 2010/0068676 A1 | 3/2010 | Mason et al. |
| 2010/0075268 A1 | 3/2010 | Duran Von Arx |
| 2010/0086890 A1 | 4/2010 | Kuo |
| 2010/0138025 A1 | 6/2010 | Morton et al. |
| 2010/0142789 A1 | 6/2010 | Chang et al. |
| 2010/0145664 A1 | 6/2010 | Hultgren et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0179789 A1 | 7/2010 | Sachdeva et al. |
| 2010/0193482 A1 | 8/2010 | Ow et al. |
| 2010/0196837 A1 | 8/2010 | Farrell |
| 2010/0216085 A1 | 8/2010 | Kopelman |
| 2010/0217130 A1 | 8/2010 | Weinlaender |
| 2010/0231577 A1 | 9/2010 | Kim et al. |
| 2010/0268363 A1 | 10/2010 | Karim et al. |
| 2010/0268515 A1 | 10/2010 | Vogt et al. |
| 2010/0279243 A1 | 11/2010 | Cinader et al. |
| 2010/0280798 A1 | 11/2010 | Pattijn |
| 2010/0281370 A1 | 11/2010 | Rohaly et al. |
| 2010/0303316 A1 | 12/2010 | Bullis et al. |
| 2010/0312484 A1 | 12/2010 | DuHamel et al. |
| 2010/0327461 A1 | 12/2010 | Co et al. |
| 2011/0007920 A1 | 1/2011 | Abolfathi et al. |
| 2011/0012901 A1 | 1/2011 | Kaplanyan |
| 2011/0027743 A1 | 2/2011 | Cinader, Jr. et al. |
| 2011/0045428 A1 | 2/2011 | Boltunov et al. |
| 2011/0056350 A1 | 3/2011 | Gale et al. |
| 2011/0081625 A1 | 4/2011 | Fuh |
| 2011/0091832 A1 | 4/2011 | Kim et al. |
| 2011/0102549 A1 | 5/2011 | Takahashi |
| 2011/0102566 A1 | 5/2011 | Zakian et al. |
| 2011/0104630 A1 | 5/2011 | Matov et al. |
| 2011/0136072 A1 | 6/2011 | Li et al. |
| 2011/0136090 A1 | 6/2011 | Kazemi |
| 2011/0143300 A1 | 6/2011 | Villaalba |
| 2011/0143673 A1 | 6/2011 | Landesman et al. |
| 2011/0159452 A1 | 6/2011 | Huang |
| 2011/0164810 A1 | 7/2011 | Zang et al. |
| 2011/0207072 A1 | 8/2011 | Schiemann |
| 2011/0212420 A1 | 9/2011 | Vuillemot |
| 2011/0220623 A1 | 9/2011 | Beutler |
| 2011/0235045 A1 | 9/2011 | Koerner et al. |
| 2011/0240064 A1 | 10/2011 | Wales et al. |
| 2011/0262881 A1* | 10/2011 | Mauclaire ............... A61C 7/00 433/140 |
| 2011/0269092 A1 | 11/2011 | Kuo et al. |
| 2011/0316994 A1 | 12/2011 | Lemchen |
| 2012/0028210 A1 | 2/2012 | Hegyi et al. |
| 2012/0029883 A1 | 2/2012 | Heinz et al. |
| 2012/0040311 A1 | 2/2012 | Nilsson |
| 2012/0064477 A1 | 3/2012 | Schmitt |
| 2012/0081786 A1 | 4/2012 | Mizuyama et al. |
| 2012/0086681 A1 | 4/2012 | Kim et al. |
| 2012/0115107 A1 | 5/2012 | Adams |
| 2012/0129117 A1 | 5/2012 | McCance |
| 2012/0147912 A1 | 6/2012 | Moench et al. |
| 2012/0150494 A1 | 6/2012 | Anderson et al. |
| 2012/0166213 A1 | 6/2012 | Arnone et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0029284 A1 | 1/2013 | Teasdale |
| 2013/0081272 A1 | 4/2013 | Johnson et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0163627 A1 | 6/2013 | Seurin et al. |
| 2013/0201488 A1 | 8/2013 | Ishihara |
| 2013/0204599 A1 | 8/2013 | Matov et al. |
| 2013/0209952 A1 | 8/2013 | Kuo et al. |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0278396 A1 | 10/2013 | Kimmel |

(56) References Cited

U.S. PATENT DOCUMENTS

| | | |
|---|---|---|
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2013/0325431 A1 | 12/2013 | See et al. |
| 2013/0337412 A1 | 12/2013 | Kwon |
| 2014/0061974 A1 | 3/2014 | Tyler |
| 2014/0081091 A1 | 3/2014 | Abolfathi et al. |
| 2014/0093160 A1 | 4/2014 | Porikli et al. |
| 2014/0100495 A1* | 4/2014 | Haseley ............... A61H 1/008 601/37 |
| 2014/0106289 A1 | 4/2014 | Kozlowski |
| 2014/0122027 A1 | 5/2014 | Andreiko et al. |
| 2014/0136222 A1 | 5/2014 | Arnone et al. |
| 2014/0142902 A1 | 5/2014 | Chelnokov et al. |
| 2014/0178829 A1 | 6/2014 | Kim |
| 2014/0220520 A1* | 8/2014 | Salamini ............... A61B 5/103 434/185 |
| 2014/0265034 A1 | 9/2014 | Dudley |
| 2014/0272774 A1 | 9/2014 | Dillon et al. |
| 2014/0280376 A1 | 9/2014 | Kuo |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0342299 A1 | 11/2014 | Jung |
| 2014/0342301 A1 | 11/2014 | Fleer et al. |
| 2014/0350354 A1 | 11/2014 | Stenzler et al. |
| 2014/0363778 A1 | 12/2014 | Parker |
| 2015/0002649 A1 | 1/2015 | Nowak et al. |
| 2015/0004553 A1 | 1/2015 | Li et al. |
| 2015/0021210 A1 | 1/2015 | Kesling |
| 2015/0031940 A1* | 1/2015 | Floyd ............... A61F 5/58 600/24 |
| 2015/0079530 A1* | 3/2015 | Bergersen ............... A61C 7/08 433/6 |
| 2015/0079531 A1 | 3/2015 | Heine |
| 2015/0094564 A1 | 4/2015 | Tashman et al. |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0132708 A1 | 5/2015 | Kuo |
| 2015/0140502 A1 | 5/2015 | Brawn et al. |
| 2015/0150501 A1 | 6/2015 | George et al. |
| 2015/0164335 A1 | 6/2015 | Van Der Poel et al. |
| 2015/0173856 A1 | 6/2015 | Iowe et al. |
| 2015/0182303 A1 | 7/2015 | Abraham et al. |
| 2015/0216626 A1 | 8/2015 | Ranjbar |
| 2015/0216716 A1 | 8/2015 | Anitua Aldecoa |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0320532 A1 | 11/2015 | Matty et al. |
| 2015/0325044 A1 | 11/2015 | Lebovitz |
| 2015/0338209 A1 | 11/2015 | Knüttel |
| 2015/0351638 A1 | 12/2015 | Amato |
| 2015/0374469 A1 | 12/2015 | Konno et al. |
| 2016/0000332 A1 | 1/2016 | Atiya et al. |
| 2016/0003610 A1 | 1/2016 | Lampert et al. |
| 2016/0042509 A1 | 2/2016 | Andreiko et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0095668 A1 | 4/2016 | Kuo et al. |
| 2016/0100924 A1 | 4/2016 | Wilson et al. |
| 2016/0106520 A1 | 4/2016 | Borovinskih et al. |
| 2016/0120621 A1 | 5/2016 | Li et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0220105 A1 | 8/2016 | Durent |
| 2016/0220200 A1 | 8/2016 | Sandholm et al. |
| 2016/0225151 A1 | 8/2016 | Cocco et al. |
| 2016/0228213 A1 | 8/2016 | Tod et al. |
| 2016/0242871 A1 | 8/2016 | Morton et al. |
| 2016/0246936 A1 | 8/2016 | Kahn |
| 2016/0287358 A1 | 10/2016 | Nowak et al. |
| 2016/0296303 A1 | 10/2016 | Parker |
| 2016/0302885 A1 | 10/2016 | Matov et al. |
| 2016/0328843 A1 | 11/2016 | Graham et al. |
| 2016/0338799 A1 | 11/2016 | Wu et al. |
| 2016/0346063 A1 | 12/2016 | Schulhof et al. |
| 2016/0367339 A1 | 12/2016 | Khardekar et al. |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0049311 A1 | 2/2017 | Borovinskih et al. |
| 2017/0049326 A1 | 2/2017 | Alfano et al. |
| 2017/0056131 A1 | 3/2017 | Alauddin et al. |
| 2017/0071705 A1 | 3/2017 | Kuo |
| 2017/0079747 A1 | 3/2017 | Graf et al. |
| 2017/0086943 A1 | 3/2017 | Mah |
| 2017/0100209 A1 | 4/2017 | Wen |
| 2017/0100212 A1 | 4/2017 | Sherwood et al. |
| 2017/0100213 A1 | 4/2017 | Kuo |
| 2017/0100214 A1 | 4/2017 | Wen |
| 2017/0105815 A1 | 4/2017 | Matov et al. |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0215739 A1 | 8/2017 | Miyasato |
| 2017/0251954 A1 | 9/2017 | Lotan et al. |
| 2017/0258555 A1 | 9/2017 | Kopelman |
| 2017/0265967 A1* | 9/2017 | Hong ............... A61C 7/002 |
| 2017/0265970 A1 | 9/2017 | Verker |
| 2017/0319054 A1 | 11/2017 | Miller et al. |
| 2017/0319296 A1 | 11/2017 | Webber et al. |
| 2017/0325690 A1 | 11/2017 | Salah et al. |
| 2017/0340411 A1 | 11/2017 | Akselrod |
| 2017/0340415 A1 | 11/2017 | Choi et al. |
| 2018/0000563 A1 | 1/2018 | Shanjani et al. |
| 2018/0000565 A1 | 1/2018 | Shanjani et al. |
| 2018/0028063 A1 | 2/2018 | Elbaz et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0071054 A1 | 3/2018 | Ha |
| 2018/0071055 A1 | 3/2018 | Kuo |
| 2018/0085059 A1 | 3/2018 | Lee |
| 2018/0096465 A1 | 4/2018 | Levin |
| 2018/0168788 A1 | 6/2018 | Fernie |
| 2018/0228359 A1 | 8/2018 | Meyer et al. |
| 2018/0280125 A1 | 10/2018 | Longley et al. |
| 2018/0318042 A1 | 11/2018 | Baek et al. |
| 2018/0318043 A1 | 11/2018 | Li et al. |
| 2018/0368944 A1 | 12/2018 | Sato et al. |
| 2019/0026599 A1 | 1/2019 | Salah et al. |
| 2019/0046296 A1 | 2/2019 | Kopelman et al. |
| 2019/0046297 A1 | 2/2019 | Kopelman et al. |
| 2019/0069975 A1 | 3/2019 | Cam et al. |
| 2019/0076216 A1 | 3/2019 | Moss et al. |
| 2019/0090983 A1 | 3/2019 | Webber et al. |
| 2019/0171618 A1 | 6/2019 | Kuo |
| 2019/0314119 A1 | 10/2019 | Kopelman et al. |
| 2020/0046463 A1 | 2/2020 | Kimura et al. |

FOREIGN PATENT DOCUMENTS

| | | |
|---|---|---|
| AU | 5598894 A | 6/1994 |
| CA | 1121955 A1 | 4/1982 |
| CN | 1655732 A | 8/2005 |
| CN | 1655733 A | 8/2005 |
| CN | 102017658 A | 4/2011 |
| CN | 103889364 A | 6/2014 |
| CN | 204092220 U | 1/2015 |

(56) References Cited

FOREIGN PATENT DOCUMENTS

| | | |
|---|---|---|
| CN | 105496575 A | 4/2016 |
| CN | 105997274 A | 10/2016 |
| DE | 2749802 A1 | 5/1978 |
| DE | 3526198 A1 | 2/1986 |
| DE | 4207169 A1 | 9/1993 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 202012011899 U1 | 1/2013 |
| DE | 102014225457 A1 | 6/2016 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2867377 A1 | 9/2005 |
| FR | 2930334 A1 | 10/2009 |
| GB | 1550777 A | 8/1979 |
| JP | 53-058191 A | 5/1978 |
| JP | 4028359 A | 1/1992 |
| JP | 08-508174 A | 9/1996 |
| JP | 09-19443 A | 1/1997 |
| JP | 2003245289 A | 9/2003 |
| JP | 2000339468 A | 9/2004 |
| JP | 2005527320 A | 9/2005 |
| JP | 2005527321 A | 9/2005 |
| JP | 2006043121 A | 2/2006 |
| JP | 2007151614 A | 6/2007 |
| JP | 2007260158 A | 10/2007 |
| JP | 2007537824 A | 12/2007 |
| JP | 2008067732 A | 3/2008 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009078133 A | 4/2009 |
| JP | 2009101386 A | 5/2009 |
| JP | 2009205330 A | 9/2009 |
| JP | 2010017726 A | 1/2010 |
| JP | 2011087733 A | 5/2011 |
| JP | 2012045143 A | 3/2012 |
| JP | 2013007645 A | 1/2013 |
| JP | 2013192865 A | 9/2013 |
| JP | 201735173 A | 2/2017 |
| KR | 10-20020062793 A | 7/2002 |
| KR | 10-20070108019 A | 11/2007 |
| KR | 10-20090065778 A | 6/2009 |
| KR | 10-1266966 B1 | 5/2013 |
| KR | 10-2016-041632 A | 4/2016 |
| KR | 10-2009-0071127 A | 6/2016 |
| KR | 10-1675089 B1 | 11/2016 |
| TW | 480166 B | 3/2002 |
| WO | WO91/004713 | 4/1991 |
| WO | WO92/03102 A1 | 3/1992 |
| WO | WO94/010935 A1 | 5/1994 |
| WO | WO96/23452 A1 | 8/1996 |
| WO | WO98/032394 A1 | 7/1998 |
| WO | WO98/044865 A1 | 10/1998 |
| WO | WO01/08592 A1 | 2/2001 |
| WO | WO01/85047 A2 | 11/2001 |
| WO | WO02/017776 A2 | 3/2002 |
| WO | WO02/062252 A1 | 8/2002 |
| WO | WO02/095475 A1 | 11/2002 |
| WO | WO03/003932 A2 | 1/2003 |
| WO | WO2006/096558 A2 | 9/2006 |
| WO | WO2006/100700 A1 | 9/2006 |
| WO | WO2006/133548 A1 | 12/2006 |
| WO | WO2007/019709 A2 | 2/2007 |
| WO | WO2007/071341 A1 | 6/2007 |
| WO | WO2007/103377 A2 | 9/2007 |
| WO | WO2008/115654 A1 | 9/2008 |
| WO | WO2009/016645 A2 | 2/2009 |
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/059988 A1 | 5/2010 |
| WO | WO2010/123892 A1 | 10/2010 |
| WO | WO2012/007003 A1 | 1/2012 |
| WO | WO2012/064684 A2 | 5/2012 |
| WO | WO2012/074304 A2 | 6/2012 |
| WO | WO2012/078980 A2 | 6/2012 |
| WO | WO2012/083968 A1 | 6/2012 |
| WO | WO2012/140021 A2 | 10/2012 |
| WO | WO2013/058879 A2 | 4/2013 |
| WO | WO 2014/068107 A1 | 5/2014 |
| WO | WO2014/091865 A1 | 6/2014 |
| WO | WO2014/143911 A1 | 9/2014 |
| WO | WO2015/015289 A2 | 2/2015 |
| WO | WO2015/063032 A1 | 5/2015 |
| WO | WO2015/112638 A1 | 7/2015 |
| WO | WO2015/176004 A1 | 11/2015 |
| WO | WO2016/004415 A1 | 1/2016 |
| WO | WO2016/028106 A1 | 2/2016 |
| WO | WO2016/042393 A1 | 3/2016 |
| WO | WO2016/061279 A1 | 4/2016 |
| WO | WO2016/084066 A1 | 6/2016 |
| WO | WO2016/099471 A1 | 6/2016 |
| WO | WO2016/113745 A1 | 7/2016 |
| WO | WO2016/116874 A1 | 7/2016 |
| WO | WO2016/200177 A1 | 12/2016 |
| WO | WO2017/006176 A1 | 1/2017 |
| WO | WO2017/182654 A1 | 10/2017 |
| WO | WO2018/057547 A1 | 3/2018 |
| WO | WO2018/085718 A2 | 5/2018 |
| WO | WO2018/232113 A1 | 12/2018 |
| WO | WO2019/018784 A1 | 1/2019 |

OTHER PUBLICATIONS

Bandodkar et al.; All-printed magnetically self-healing electrochemical devices; Science Advances; 2(11); 11 pages; e1601465; Nov. 2016.

Bandodkar et al.; Self-healing inks for autonomous repair of printable electrochemical devices; Advanced Electronic Materials; 1(12); 5 pages; 1500289; Dec. 2015.

Bandodkar et al.; Wearable biofuel cells: a review; Electroanalysis; 28 (6); pp. 1188-1200; Jun. 2016.

Bandodkar et al.; Wearable chemical sensors: present challenges and future prospects; Acs Sensors; 1(5); pp. 464-482; May 11, 2016.

Imani et al.; A wearable chemical-electrophysiological hybrid biosensing system for real-time health and fitness monitoring; Nature Communications; 7; 11650. doi 1038/ncomms11650; 7 pages; May 23, 2016.

Jia et al.; Epidermal biofuel cells: energy harvesting from human perspiration; Angewandle Chemie International Edition; 52(28); pp. 7233-7236; Jul. 8, 2013.

Jia et al.; Wearable textile biofuel cells for powering electronics; Journal of Materials Chemistry A; 2(43); pp. 18184-18189; Oct. 14, 2014.

Jeerapan et al.; Stretchable biofuel cells as wearable textile-based self-powered sensors; Journal of Materials Chemistry A; 4(47); pp. 18342-18353; Dec. 21, 2016.

Kim et al.; Advanced materials for printed wearable electrochemical devices: A review; Advanced Electronic Materials; 3(1); 15 pages; 1600260; Jan. 2017.

Kim et al.; Noninvasive alcohol monitoring using a wearable tatto-based iontophoretic-biosensing system; Acs Sensors; 1(8); pp. 1011-1019; Jul. 22, 2016.

(56) References Cited

OTHER PUBLICATIONS

Kim et al.; Non-invasive mouthguard biosensor for continuous salivary monitoring of metabolites; Analyst; 139(7); pp. 1632-1636; Apr. 7, 2014.

Kim et al.; A wearable fingernail chemical sensing platform: pH sensing at your fingertips; Talanta; 150; pp. 622-628; Apr. 2016.

Kim et al.; Wearable salivary uric acid mouthguard biosensor with integrated wireless electronics; Biosensors and Bioelectronics; 74; pp. 1061-1068; 19 pages; (Author Manuscript); Dec. 2015.

Kumar et al.; All-printed, stretchable Zn—Ag2o rechargeable battery via, hyperelastic binder for self-powering wearable electronics; Advanced Energy Materials; 7(8); 8 pages; 1602096; Apr. 2017.

Kumar et al.; Biomarkers in orthodontic tooth movement; Journal of Pharmacy Bioallied Sciences; 7(Suppl 2); pp. S325-S330; 12 pages; (Author Manuscript); Aug. 2015.

Parrilla et al.; A textile-based stretchable multi-ion potentiometric sensor; Advanced Healthcare Materials; 5(9); pp. 996-1001; May 2016.

Windmiller et al.; Wearable electrochemical sensors and biosensors: a , review; Electroanalysis; 25(1); pp. 29-46; Jan. 2013.

Zhou et al.; Bio-logic analysis of injury biomarker patterns in human serum samples; Talanta; 83(3); pp. 955-959; Jan. 15, 2011.

Zhou et al.; Biofuel cells for self-powered electrochemical biosensing and logic biosensing: A review; Electroanalysis; 24(2); pp. 197-209; Feb. 2012.

Kopelman et al.; U.S. Appl. No. 16/152,281 entitled "Intraoral appliances for sampling soft-tissue," filed Oct. 4, 2018.

Morton et al.; U.S. Appl. No. 16/177,067 entitled "Dental appliance having selective occlusal loading and controlled intercuspation," filed Oct. 31, 2018.

Akopov et al.; U.S. Appl. No. 16/178,491 entitled "Automatic treatment planning," filed Nov. 1, 2018.

Elbaz et al.; U.S. Appl. No. 16/198,488 entitled "Intraoral scanner with dental diagnostics capabilities," filed Nov. 21, 2018.

Elbaz et al.; U.S. Appl. No. 16/188,262 entitled "Intraoral scanner with dental diagnostics capabilities," filed Nov. 12, 2018.

AADR. American Association for Dental Research; Summary of Activities; Los Angeles, CA; p. 195; Mar. 20-23,(year of pub. sufficiently earlier than effective US filing date and any foreign priority date) 1980.

Alcaniz et aL; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.

Alexander et al.; The DigiGraph Work Station Part 2 Clinical Management; J. Clin. Orthod.; pp. 402-407; (Author Manuscript); Jul. 1990.

Allesee Orthodontic Appliance: Important Tip About Wearing the Red White & Blue Active Clear Retainer System; Allesee Orthodontic Appliances—Pro Lab; 1 page; (year of pub. sufficiently earlier than effective US filing date and any foreign priority date); 1998.

Allesee Orthodontic Appliances: DuraClearTM; Porduct information; 1 page; (year of pub. sufficiently earlier than effective US filing date and any foreign priority date) 1997.

Allesee Orthodontic Appliances; The Choice Is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.

Allesee Orthodontic Appliances; The Choice Is Clear: Red, White & Blue . . . The Simple, Affordable, No-Braces Treatment; p(roduct information), 6 pages; (year of pub. sufficiently earlier than effective US filing date and any foreign priority date) 2003.

Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.

Allesee Orthodontic Appliances; The Red, White & Blue Way to Improve Your Smile; (information for patients), 2 pages; (year of pub. sufficiently earlier than effective US filing date and any foreign priority date) 1992.

Allesee Orthodontic Appliances; You may be a candidate for this invisible no-braces treatment; product information for patients; 2 pages; (year of pub. sufficiently earlier than effective US filing date and any foreign priority date) 2002.

Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.

Altschuler et al.; Laser Electro-Optic System for Rapid Three-Dimensional (3D) Topographic Mapping of Surfaces; Optical Engineering; 20(6); pp. 953-961; Dec. 1981.

Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.

Altschuler; 3D Mapping of Maxillo-Facial Prosthesis; AADR Abstract #607; 2 pages total, (year of pub. sufficiently earlier than effective US filing date and any foreign priority date) 1980.

Andersson et al.; Clinical Results with Titanium Crowns Fabricated with Machine Duplication and Spark Erosion; Acta Odontologica Scandinavica; 47(5); pp. 279-286; Oct. 1989.

Andrews, The Six Keys to Optimal Occlusion Straight Wire, Chapter 3, L.A. Wells; pp. 13-24; (year of pub. sufficiently earlier than effective US filing date and any foreign priority date) 1989.

Barone et al.; Creation of 3D multi-body orthodontic models by using independent imaging sensors; Sensors; 13(2); pp. 2033-2050; Feb. 5, 2013.

Bartels et al.; An Introduction to Splines for Use in Computer Graphics and Geometric Modeling; Morgan Kaufmann Publishers; pp. 422-425 Jan. 1, 1987.

Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.

Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.

Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.

Baumrind; Integrated Three-Dimensional Craniofacial Mapping: Background, Principles, and Perspectives; Seminars in Orthodontics; 7(4); pp. 223-232; Dec. 2001.

Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.

Bhatia et al.; A Computer-Aided Design for Orthognathic Surgery; British Journal of Oral and Maxillofacial Surgery; 22(4); pp. 237-253; Aug. 1, 1984.

Biggerstaff et al.; Computerized Analysis of Occlusion in the Postcanine Dentition; American Journal of Orthodontics; 61(3); pp. 245-254; Mar. 1972.

Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.

Bourke, Coordinate System Transformation; 1 page; retrived from the internet (http://astronomy.swin.edu.au/' pbourke/prolection/coords) on Nov. 5, 2004; Jun. 1996.

Boyd et al.; Three Dimensional Diagnosis and Orthodontic Treatment of Complex Malocclusions With the lnvisalipn Appliance; Seminars in Orthodontics; 7(4); pp. 274-293; Dec. 2001.

(56) References Cited

OTHER PUBLICATIONS

Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on the Uses of the Computer in Orthodontic Practice (Part 1); Journal of Clinical Orthodontics; 13(7); pp. 442-453; (interview); Jul. 1979.
Burstone; Dr. Charles J. Burstone on the Uses of the Computer in Orthodontic Practice (Part 2); journal of Clinical Orthodontics; 13(8); pp. 539-551 (interview); Aug. 1979.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
Cottingham; Gnathologic Clear Plastic Positioner; American Journal of Orthodontics; 55(1); pp. 23-31; Jan. 1969.
Crawford; CAD/CAM in the Dental Office: Does It Work?; Canadian Dental Journal; 57(2); pp. 121-123 Feb. 1991.
Crawford; Computers in Dentistry: Part 1: CAD/CAM: The Computer Moves Chairside, Part 2: F. Duret ' A Man With a Vision, Part 3: The Computer Gives New Vision—Literally, Part 4: Bytes 'N Bites The Computer Moves From the Front Desk to the Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
Cureton; Correcting Malaligned Mandibular Incisors with Removable Retainers; Journal of Clinical Orthodontics; 30(7); pp. 390-395; Jul. 1996.
Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
DCS Dental AG; The CAD/CAM 'DCS Titan System' for Production of Crowns/Bridges; DSC Production; pp. 1-7; Jan. 1992.
Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filing date and any foreign priority date) 1992.
Dent-X; Dentsim . . . Dent-x's virtual reality 3-D training simulator . . . A revolution in dental education; 6 pages; retrieved from the internet (http://www.dent-x.com/DentSim.htm); on Sep. 24, 1998.

Doyle; Digital Dentistry; Computer Graphics World; pp. 50-52 andp. 54; Oct. 2000.
Duret et al.; CAD/CAM Imaging in Dentistry; Current Opinion in Dentistry; 1(2); pp. 150-154; Apr. 1991.
Duret et al; CAD-CAM in Dentistry; Journal of the American Dental Association; 117(6); pp. 715-720; Nov. 1988.
Duret; The Dental CAD/CAM, General Description of the Project; Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Economides; The Microcomputer in the Orthodontic Office; Journal of Clinical Orthodontics; 13(11); pp. 767-772; Nov. 1979.
Elsasser; Some Observations on the History and Uses of the Kesling Positioner; American Journal of Orthodontics; 36(5); pp. 368-374; May 1, 1950.
English translation of Japanese Laid-Open Publication No. 63-11148 to inventor T. Ozukuri (Laid-Open on Jan. 18, 1998) pp. 1-7.
Faber et al.; Computerized Interactive Orthodontic Treatment Planning; American Journal of Orthodontics; 73(1); pp. 36-46; Jan. 1978.
Felton et al.; A Computerized Analysis of the Shape and Stability of Mandibular Arch Form; American Journal of Orthodontics and Dentofacial Orthopedics; 92(6); pp. 478-483; Dec. 1987.
Friede et al.; Accuracy of Cephalometric Prediction in Orthognathic Surgery; Journal of Oral and Maxillofacial Surgery; 45(9); pp. 754-760; Sep. 1987.
Futterling et al.; Automated Finite Element Modeling of a Human Mandible with Dental Implants; JS WSCG '98 -Conference Program; 8 pages; retrieved from the Internet (https://dspace5.zcu.cz/bitstream/11025/15851/1/Strasser_98.pdf); on Aug. 21, 2018.
Gim-Alldent Deutschland, "Das DUX System: Die Technik," 3 pages; (English Translation Included); (year of pub. sufficiently earlier than effective US filing date and any foreign priority date); 2002.
Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the Internet (http://www.jco-online.com/archive/print_article.asp?Year=1982&Month=06&ArticleNum+); 21 pages; Jun. 1982.
Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.
Guess et al.; Computer Treatment Estimates in Orthodontics and Orthognathic Surgery; Journal of Clinical Orthodontics; 23(4); pp. 262- 268; 11 pages; (Author Manuscript); Apr. 1989.
Heaven et al.; Computer-Based Image Analysis of Artificial Root Surface Caries; Abstracts of Papers #2094; Journal of Dental Research; 70:528; (Abstract Only); Apr. 17-21, 1991.
Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa..); on Nov. 5, 2004.
Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Inclused); Feb. 1987.
Hoffmann et al.; Role of Cephalometry for Planning of Jaw Orthopedics and Jaw Surgery Procedures; lnformatbnen, pp. 375-396; (English Abstract Included); Mar. 1991.
Hojjatie et al.; Three-Dimensional Finite Element Analysis of Glass-Ceramic Dental Crowns; Journal of Biomechanics; 23(11); pp. 1157-1166; Jan. 1990.
Huckins; CAD-CAM Generated Mandibular Model Prototype from MRI Data; AAOMS, p. 96; (Abstract Only); (year of pub. sufficiently earlier than effective US filing date and any foreign priority date) 1999.
JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.

(56) References Cited

OTHER PUBLICATIONS

JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.
Jerrold; The Problem, Electronic Data Transmission and the Law; American Journal of Orthodontics and Dentofacial Orthopedics; 113(4); pp. 478-479; 5 pages; (Author Manuscript); Apr. 1998.
Jones et al.; An Assessment of the Fit of a Parabolic Curve to Pre- and Post-Treatment Dental Arches; British Journal of Orthodontics; 16(2); pp. 85-93; May 1989.
Kesling et al.; The Philosophy of the Tooth Positioning Appliance; American Journal of Orthodontics and Oral surgery; 31(6); pp. 297-304; Jun. 1945.
Kesling; Coordinating the Predetermined Pattern and Tooth Positioner with Conventional Treatment; American Journal of Orthodontics and Oral Surgery; 32(5); pp. 285-293; May 1946.
Kleeman et al.; The Speed Positioner; J. Clin. Orthod.; 30(12); pp. 673-680; Dec. 1996.
Kuroda et al.; Three-Dimensional Dental Cast Analyzing System Using Laser Scanning; American Journal of Orthodontics and Dentofacial Orthopedics; 110(4); pp. 365-369; Oct. 1996.
Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.
Leinfelder et al.; A New Method for Generating Ceramic Restorations: a CAD-CAM System; Journal of the American Dental Association; 118(6); pp. 703-707; Jun. 1989.
Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.
McCann; Inside the ADA; J. Amer. Dent. Assoc, 118:286-294; Mar. 1989.
McNamara et al.; Invisible Retainers; J. Clin Orthod.; pp. 570-578; 11 pages; (Author Manuscript); Aug. 1985.
McNamara et al.; Orthodontic and Orthopedic Treatment in the Mixed Dentition; Needham Press; pp. 347-353; Jan. 1993.
Moermann et al, Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.
Moles; Correcting Mild Malalignments—As Easy As One, Two, Three; AOA/Pro Corner; 11(2); 2 pages; (year of pub. sufficiently earlier than effective US filing date and any foreign priority date) 2002.
Mormann et al.; Marginale Adaptation von adhasuven Porzellaninlays in vitro; Separatdruck aus:Schweiz. Mschr. Zahnmed.; 95; pp. 1118-1129; 8 pages; (Macine Translated English Abstract); (year of pub. sufficiently earlier than effective US filing date and any foreign priority date); 1985.
Nahoum; The Vacuum Formed Dental Contour Appliance; N. Y. State Dent. J.; 30(9); pp. 385-390; Nov. 1964.
Nash; CEREC CAD/CAM Inlays: Aesthetics and Durability in a Single Appointment; Dentistry Today; 9(8); pp. 20, 22-23 and 54; Oct. 1990.
Ogawa et al.; Mapping, profiling and clustering of pressure pain threshold (PPT) in edentulous oral muscosa; Journal of Dentistry; 32(3); pp. 219-228; Mar. 2004.
Ogimoto et al.; Pressure-pain threshold determination in the oral mucosa; Journal of Oral Rehabilitation; 29(7); pp. 620-626; Jul. 2002.
Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.
Pinkham; Foolish Concept Propels Technology; Dentist, 3 pages, Jan./Feb. 1989.

Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 ' Abstract Collection; 23 pages; (year of pub. sufficiently earlier than effective US filing date and any foreign priority date) 1993.
Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD-CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of a 3D Cast Analysis System; British Journal of Orthodontics; 13(1); pp. 53-54; Jan. 1986.
Richmond; Recording the Dental Cast in Three Dimensions; American Journal of Orthodontics and Dentofacial Orthopedics; 92(3); pp. 199-206; Sep. 1987.
Rudge; Dental Arch Analysis: Arch Form, A Review of the Literature; The European Journal of Orthodontics; 3(4); pp. 279-284; Jan. 1981.
Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.
Shilliday; Minimizing finishing problems with the mini-positioner; American Journal of Orthodontics; 59(6); pp. 596-599; Jun. 1971.
Shimada et al.; Application of optical coherence tomography (OCT) for diagnosis of caries, cracks, and defects of restorations; Current Oral Health Reports; 2(2); pp. 73-80; Jun. 2015.
Siemens; CEREC—Computer-Reconstruction, High Tech in der Zahnmedizin; 15 pagesl; (Includes Machine Translation); (year of pub. sufficiently earlier than effective US filing date and any foreign priority date); 2004.

(56) References Cited

OTHER PUBLICATIONS

Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.

Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.

The American Heritage, Stedman's Medical Dictionary; Gingiva; 3 pages; retrieved from the interent (http://reference.com/search/search?q=gingiva) on Nov. 5, 2004.

The Dental Company Sirona: Cerc omnicam and cerec bluecam brochure: The first choice in every case; 8 pages; (year of pub. sufficiently earlier than effective US filing date and any foreign priority date) 2014.

Thorlabs; Pellin broca prisms; 1 page; retrieved from the internet (www.thorlabs.com); Nov. 30, 2012.

Tiziani et al.; Confocal principle for macro and microscopic surface and defect analysis; Optical Engineering; 39(1); pp. 32-39; Jan. 1, 2000.

Truax; Truax Clasp-Less(TM) Appliance System; The Functional Orthodontist; 9(5); pp. 22-24, 26-8; Sep.-Oct. 1992.

Tru-Tatn Orthodontic & Dental Supplies, Product Brochure, Rochester, Minnesota 55902, 16 pages; (year of pub. sufficiently earlier than effective US filing date and any foreign priority date) 1996.

U.S. Department of Commerce, National Technical Information Service, Holodontography: An Introduction to Dental Laser Holography; School of Aerospace Medicine Brooks AFB Tex; Mar. 1973, 40 pages; Mar. 1973.

U.S. Department of Commerce, National Technical Information Service; Automated Crown Replication Using Solid Photography SM; Solid Photography Inc., Melville NY,; 20 pages; Oct. 1977.

Van Der Linden et al.; Three-Dimensional Analysis of Dental Casts by Means of the Optocom; Journal of Dental Research; 51(4); p. 1100; Jul.-Aug. 1972.

Van Hilsen et al.; Comparing potential early caries assessment methods for teledentistry; BMC Oral Health; 13(16); doi: 10.1186/1472-6831-13-16; 9 pages; Mar. 2013.

Varady et al.; Reverse Engineering of Geometric Models'An Introduction; Computer-Aided Design; 29(4); pp. 255-268; 20 pages; (Author Manuscript); Apr. 1997.

Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.

Warunek et.al.; Clinical Use of Silicone Elastomer Applicances; JCO; 23 (10); pp. 694-700; Oct. 1989.

Wells; Application of the Positioner Appliance in Orthodontic Treatment; American Journal of Orthodontics; 58(4); pp. 351-366; Oct. 1970.

Williams; The Switzerland and Minnesota Developments in CAD/CAM; Journal of Dental Practice Administration; 4(2); pp. 50-55; Apr./Jun. 1987.

Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.

WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.

Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.

Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.

Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.

Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.

Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.

Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.

Doruk et al.; The role of the headgear timer in extraoral co-operation; European Journal of Orthodontics; 26; pp. 289-291; Jun. 1, 2004.

Friedrich et al; Measuring system for in vivo recording of force systems in orthodontic treatment-concept and analysis of accuracy; J. Biomech.; 32(1); pp. 81-85; (Abstract Only) Jan. 1999.

Grest, Daniel; Marker-Free Human Motion Capture in Dynamic Cluttered Environments from a Single View-Point, PhD Thesis; 171 pages; Dec. 2007.

Invisalign; You were made to move. There's never been a better time to straighten your teeth with the most advanced clear aligner in the world; Product webpage; 2 pages; retrieved from the internet (www.invisalign.com/) on Dec. 28, 2017.

Kumar et al.; Rapid maxillary expansion: A unique treatment modality in dentistry; J. Clin. Diagn. Res.; 5(4); pp. 906-911; Aug. 2011.

Nedelcu et al.; "Scanning Accuracy and Precision in 4 Intraoral Scanners: An In Vitro Comparison Based on 3-Dimensional Analysis"; J. Prosthet. Dent.; 112(6); pp. 1461-71; Dec. 2014.

Sahm et al.; "Micro-Electronic Monitoring of Functional Appliance Wear"; Eur J Orthod.; 12(3); pp. 297-301; Aug. 1990.

Sahm; Presentation of a wear timer for the clarification of scientific questions in orthodontic orthopedics; Fortschritte der Kieferorthopadie; 51 (4); pp. 243-247; (Translation Included) Jul. 19990.

Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.

Thera Mon; "Microsensor"; "2 pages"; retrieved from the interent (www.english.thera-mon.com/the-product/transponder/index.html); on Sep. 19, 2016.

Wikipedia; Palatal expansion; 3 pages; retrieved from the Internet (https://en.wikipedia.org/wiki/Palatal_expansion) on Mar. 5, 2018.

Wireless Sensor Networks Magazine; Embedded Teeth for Oral Activity Recognition; 2 pages; retrievedon Sep. 19, 2016 from the internet (www.wsnmagazine.com/embedded-teeth/); Jul. 29, 2013.

Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.

Carrier et al.; U.S. Appl. No. 15/803,718 entitled "Methods and apparatuses for dental images," filed Nov. 3, 2017.

Atiya et al.; U.S. Appl. No. 15/859,010 entitled "Compact confocal dental scanning apparatus," filed Dec. 29, 2017.

Shanjani et al.; U.S. Appl. No. 15/831,159 entitled "Palatal expanders and methods of expanding a palate," filed Dec. 4, 2017.

Wu et al.; U.S. Appl. No. 15/831,262 entitled "Methods and apparatuses for customizing a rapid palatal expander," filed Dec. 4, 2017.

Grove et al.; U.S. Appl. No. 15/726,243 entitled "Interproximal reduction templates," filed Oct. 5, 2017.

(56) References Cited

OTHER PUBLICATIONS

Arakawa et al; Mouthguard biosensor with telemetry system for monitoring of saliva glucose: A novel cavitas sensor; Biosensors and Bioelectronics; 84; pp. 106-111; Oct. 2016.
O'Leary et al.; U.S. Appl. No. 16/195,701 entitled "Orthodontic retainers," filed Nov. 19, 2018.
Shanjani et al., U.S. Appl. No. 16/206,894 entitled "Sensors for monitoring oral appliances," filed Nov. 28, 2019.
Shanjani et al., U.S. Appl No. 16/231,906 entitled "Augmented reality enhancements for dental practitioners." Dec. 24, 2018.
Kopleman et al., U.S. Appl. No. 16/220,381 entitled "Closed loop adaptive orthodontic treatment methods and apparatuses," Dec. 14, 2018.
beautyworlds.com; Virtual plastic surgery—beautysurge.com announces launch of cosmetic surgery digital imaging services; 5 pages; retrieved from the internet (http://www.beautyworlds.com/cosmossurgdigitalimagning.htm); Mar. 2004.
Berland; The use of smile libraries for cosmetic dentistry; Dental Tribunne: Asia pacfic Edition; pp. 16-18; Mar. 29, 2006.
Bookstein; Principal warps: Thin-plate splines and decomposition of deformations; IEEE Transactions on pattern analysis and machine intelligence; 11(6); pp. 567-585; Jun. 1989.
Cadent Inc.; OrthoCAD ABO user guide; 38 pages; Dec. 21, 2005.
Cadent Inc.; Reviewing and modifying an orthoCAD case; 4 pages; Feb. 14, 2005.
Daniels et al.; The development of the index of complexity outcome and need (ICON); British Journal of Orthodontics; 27(2); pp. 149-162; Jun. 2000.
Dentrix; Dentrix G3, new features; 2 pages; retrieved from the internet (http://www.dentrix.com/g3/new_features/index.asp); on Jun. 6, 2008.
Di Giacomo et al.; Clinical application of sterolithographic surgical guides for implant placement: Preliminary results; Journal Periodontolgy; 76(4); pp. 503-507; Apr. 2005.
Gansky; Dental data mining: potential pitfalls and practical issues; Advances in Dental Research; 17(1); pp. 109-114; Dec. 2003.
Geomagic; Dental reconstruction; 1 page; retrieved from the internet (http://geomagic.com/en/solutions/industry/detal_desc.php) on Jun. 6, 2008.
Gottschalk et al.; OBBTree: A hierarchical structure for rapid interference detection; 12 pages; (http://www.cs.unc.edu/?geom/OBB/OBBT.html); retieved from to internet (https://www.cse.iitk.ac.in/users/amit/courses/RMP/presentations/dslamba/presentation/sig96.pdf) on Apr. 25, 2019.
gpsdentaire.com; Get a realistic smile simulation in 4 steps with GPS; a smile management software; 10 pages; retrieved from the internet (http://www.gpsdentaire.com/en/preview/) on Jun. 6, 2008.
Karaman et al.; A practical method of fabricating a lingual retainer; Am. Journal of Orthodontic and Dentofacial Orthopedics; 124(3); pp. 327-330; Sep. 2003.
Mantzikos et al.; Case report: Forced eruption and implant site development; The Angle Orthodontist; 68(2); pp. 179-186; Apr. 1998.
Methot; Get the picture with a gps for smile design in 3 steps; Spectrum; 5(4); pp. 100-105; (year of pub. sufficiently earlier than effective US filing date and any foreign priority date) 2006.
OrthoCAD downloads; retrieved Jun. 27, 2012 from the internet (www.orthocad.com/download/downloads.asp); 2 pages; Feb. 14, 2005.
Page et al.; Validity and accuracy of a risk calculator in predicting periodontal disease; Journal of the American Dental Association; 133(5); pp. 569-576; May 2002.
Patterson Dental; Cosmetic imaging; 2 pages retrieved from the internet (http://patterson.eaglesoft.net/cnt_di_cosimg.html) on Jun. 6, 2008.
Rose et al.; The role of orthodontics in implant dentistry; British Dental Journal; 201(12); pp. 753-764; Dec. 23, 2006.
Rubin et al.; Stress analysis of the human tooth using a three-dimensional finite element model; Journal of Dental Research; 62(2); pp. 82-86; Feb. 1983.

Sarment et al.; Accuracy of implant placement with a sterolithographic surgical guide; journal of Oral and Maxillofacial Implants; 118(4); pp. 571-577; Jul. 2003.
Smalley; Implants for tooth movement: Determining implant location and orientation: Journal of Esthetic and Restorative Dentistry; 7(2); pp. 62-72; Mar. 1995.
Smart Technology; Smile library II; 1 page; retrieved from the internet (http://smart-technology.net/) on Jun. 6, 2008.
Smile-VISION_The smile-vision cosmetic imaging system; 2 pages; retrieved from the internet (http://www.smile-vision.net/cos_imaging.php) on Jun. 6, 2008.
Szeliski; Introduction to computer vision: Structure from motion; 64 pages; retrieved from the internet (http://robots.stanford.edu/cs223b05/notes/CS%20223-B%20L10%structurefrommotion1b.ppt, on Feb. 3, 2005.
Vevin et al.; Pose estimation of teeth through crown-shape matching; In Medical Imaging: Image Processing of International Society of Optics and Photonics; vol. 4684; pp. 955-965; May 9, 2002.
Virtual Orthodontics; Our innovative software; 2 pages; (http://www.virtualorthodontics.com/innovativesoftware.html); retrieved from the Internet (https://web.archive.org/web/20070518085145/http://www.virtualorthodontics.com/innovativesoftware.html); (year of pub. sufficiently earlier than effective US filing date and any foreign priority date) 2005.
Wiedmann; According to the laws of harmony to find the right tooth shape with assistance of the computer; Digital Dental News; 2nd Vol.; pp. 0005-0008; (English Version Included); Apr. 2008.
Wong et al.; Computer-aided design/computer-aided manufacturing surgical guidance for placement of dental implants: Case report; Implant Dentistry; 16(2); pp. 123-130; Sep. 2007.
Wang et al.; The uses of orthodontic study models in diagnosis and treatment planning; Hong Knog Dental Journal; 3(2); pp. 107-115; Dec. 2006.
Yaltara Software; Visual planner; 1 page; retrieved from the internet (http://yaltara.com/vp/) on Jun. 6, 2008.
Zhang et al.; Visual speech features extraction for improved speech recognition; 2002 IEEE International conference on Acoustics, Speech and Signal Processing; vol. 2; 4 pages; May 13-17, 2002.
Arnone et al.; U.S. Appl. No. 16/235,449 entitled "Method and system for providing indexing and cataloguing of orthodontic related treatment profiles and options," filed Dec. 28, 2018.
Mason et al.; U.S. Appl. No. 16/374,648 entitled "Dental condition evaluation and treatment," filed Apr. 3, 2019.
Brandt et al.; U.S. Appl. No. 16/235,490 entitled "Dental wire attachment," filed Dec. 28, 2018.
Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.
Alves et al.; New trends in food allergens detection: toward biosensing strategies; Critical Reviews in Food Science and Nutrition; 56(14); pp. 2304-2319; doi: 10.1080/10408398.2013.831026; Oct. 2016.
CSI Computerized Scanning and Imaging Facility; What is a maximum/minimum intensity projection (MIP/MinIP); 1 page; retrived from the internet (http://csi.whoi.edu/content/what-maximumminimum-intensity-projection-mipminip); Jan. 4, 2010.
Di Muzio et al.; Minimum intensity projection (MinIP); 6 pages; retrieved from the internet (https://radiopaedia.org/articles/minimum-intensity-projection-minip) on Sep. 6, 2018.
Ellias et al.; Proteomic analysis of saliva identifies potential biomarkers for orthodontic tooth movement; The Scientific World Journal; vol. 2012; Article ID 647240; dio:10.1100/2012/647240; 7 pages; (year of pub. sufficiently earlier than effective US filing date and any foreign priority date) 2012.
Florez-Moreno; Time-related changes in salivary levels of the osteotropic factors sRANKL and OPG through orthodontic tooth movement; American Journal of Orthodontics and Dentofacial Orthopedics; 143(1); pp. 92-100; Jan. 2013.
Sirona Dental Systems GmbH, Cerec 3D, Manuel utiiisateur, Version 2.0X (in French); 114 pages; (English translation of table of contents included); (year of pub. sufficiently earlier than effective US filing date and any foreign priority date); 2003.

(56) References Cited

OTHER PUBLICATIONS

Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.
Watson et al.; Pressures recorded at to denture base-mucosal surface interface in complete denture wearers; Journal of Oral Rehabilitation 14(6); pp. 575-589; Nov. 1987.
Wolf; Three-dimensional structure determination of semi-transparent objects from holographic data; Optics Communications; 1(4); pp. 153-156; Sep. 1969.
Riley et al.; U.S. Appl. No. 16/003,841 entitled Palatal expander with skeletal anchorage devices, filed Jun. 8, 2018.
Shanjani et al.; U.S. Appl. No. 16/019,037 entitled "Biosensor performance indicator for intraoral appliances," filed Jun. 26, 2018.
Sato et al.; U.S. Appl. No. 16/041,606 entitled "Palatal contour anchorage," filed Jul. 20, 2018.
Xue et al.; U.S. Appl. No. 16/010,087 entitled "Automatic detection of tooth type and eruption status," filed Jun. 15, 2018.
Sato et al.; U.S. Appl. No. 16/048,054 entitled "Optical coherence tomography for orthodontic aligners," filed Jul. 27, 2018.
Miller et al.; U.S. Appl. No. 16/038,088 entitled "Method and apparatuses for interactive ordering of dental aligners," filed Jul. 17, 2018.
Moalem et al.; U.S. Appl. No. 16/046,897 entitled Tooth shading, transparency and glazing, filed Jul. 26, 2018.
Nyukhtikov et al.; U.S. Appl. No. 15/998,883 entitled "Buccal corridor assessment and computation," filed Aug. 15, 2018.
Bernabe et al.; Are the lower incisors the best predictors for the unerupted canine and premolars sums? An analysis of peruvian sample; The Angle Orthodontist; 75(2); pp. 202-207; Mar. 2005.
Collins English Dictionary; Teeth (definition); 9 pages; retrieved from the internet (https:www.collinsdictionary.com/us/dictionary/english/teeth) on May 13, 2019.
Dental Monitoring; Basics: How to put the cheek retractor?; 1 page (Screenshot); retrieved from the interenet (https://www.youtube.com/watch?v=6K1HXw4Kq3c); May 27, 2016.
Dental Monitoring; Dental monitoring tutorial; 1 page (Screenshot); retrieved from the internet (https:www.youtube.com/watch?v=Dbe3udOf9_c); Mar. 18, 2015.
dictionary.com; Plural (definition); 6 pages; retrieved from the internet ( https://www.dictionary.com/browse/plural#) on May 13, 2019.
dictionary.com; Quadrant (definition); 6 pages; retrieved from the internet ( https://www.dictionary.com/browse/quadrant?s=t) on May 13, 2019.
Ecligner Selfie; Change your smile; 1 page (screenshot); retrieved from the internet (https:play.google.com/store/apps/details?id=parklict.ecligner); on Feb. 13, 2018.
Martinelli et al.; Prediction of lower permanent canine and premolars width by correlation methods; The Angle Orthodontist; 75(5); pp. 805-808; Sep. 2005.
Nourallah et al.; New regression equations for prediciting the size of unerupted canines and premolars in a contemporary population; The Angle Orthodontist; 72(3); pp. 216-221; Jun. 2002.
Paredes et al.; A new, accurate and fast digital method to predict unerupted tooth size; The Angle Orthodontist; 76(1); pp. 14-19; Jan. 2006.
Levin; U.S. Appl. No. 16/282,431 entitled "Estimating a surface texture of a tooth," filed Feb. 2, 2019.
Yamada et al.; Simulation of fan-beam type optical computed-tomography imaging of strongly scattering and weakly absorbing media; Applied Optics; 32(25); pp. 4808-4814; Sep. 1, 1993.
Begole et al.; A Computer System for the Analysis of Dental Casts; The Angle Orthodontist; 51(3); pp. 252-258; Jul. 1981.
Biggerstaff; Computerized Diagnostic Setups and Simulations; Angle Orthodontist; 40(1); pp. 28-36; Jan. 1970.
Blu et al.; Linear interpolation revitalized; IEEE Transactions on Image Processing; 13(5); pp. 710-719; May 2004.
Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.
Gao et al.; 3-D element Generation for Multi-Connected Complex Dental and Mandibular Structure; IEEE Proceedings International Workshop in Medical Imaging and Augmented reality; pp. 267-271; Jun. 12, 2001.
Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.
Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.
Kanazawa et al.; Three-Dimensional Measurements of the Occlusal Surfaces of Upper Molars in a Dutch Population; Journal of Dental Research; 63(11); pp. 1298-1301; Nov. 1984.
Kochanek; Interpolating Splines with Local Tension, Continuity and Bias Control; Computer Graphics; 18(3); pp. 33-41; Jan. 1, 1984.
Kunii et al.; Articulation Simulation for an Intelligent Dental Care System; Displays; 15(3); pp. 181-188; Jul. 1994.
Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.
Richmond et al.; The Development of the PAR Index (Peer Assessment Rating): Reliability and Validity.; The European Journal of Orthodontics; 14(2); pp. 125-139; Apr. 1992.
Sturman; Interactive Keyframe Animation of 3-D Articulated Models; Proceedings Graphics Interface '84; vol. 86; pp. 35-40; May-Jun. 1984.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.
Verstreken et al.; An Image-Guided Planning System for Endosseous Oral Implants; IEEE Transactions on Medical Imaging; 17(5); pp. 842-852; Oct. 1998.
Williams; Dentistry and CAD/CAM: Another French Revolution; J. Dent. Practice Admin.; 4(1); pp. 2-5 Jan./Mar. 1987.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.
Cramer; U.S. Appl. No. 15/937,569 entitled "Apparatuses and methods assisting in dental therapies," filed Mar. 27, 2018.
Cramer et al.; U.S. Appl. No. 15/942,341 entitled "Orthodontic appliances including at least partially un-erupted teeth and method of forming them," filed Mar. 30, 2018.
Farooq et al.; Relationship between tooth dimensions and malocclusion; JPMA: The Journal of the Pakistan Medical Association; 64(6); pp. 670-674; Jun. 2014.
Newcombe; DTAM: Dense tracking and mapping in real-time; 8 pages; retrieved from the internet (http://www.doc.ic.ac.uk/?ajd/Publications/newcombe_etal_iccv2011.pdf; on Dec. 2011.
ormco.com; Increasing clinical performance with 3D interactive treatment planning and patient-specific appliances; 8 pages; retrieved from the Internet (http://www.konsident.com/wp-content/files_mf/1295385693http_ormco.com_index_cmsfilesystemaction_fileOrmcoPDF_whitepapers.pdf) on Feb. 27, 2019.
Video of DICOM to Surgical Guides; Can be viewed at <URL:https://youtu.be/47KtOmCEFQk; Published Apr. 4, 2016.

(56) References Cited

OTHER PUBLICATIONS

Sabina et al., U.S. Appl. No. 16/258,516 entitled "Diagnostic intraoral scanning" filed Jan. 25, 2019.
Sabina et al., U.S. Appl. No. 16/258,523 entitled "Diagnostic intraoral tracking" filed Jan. 25, 2019.
Sabina et al., U.S. Appl. No. 16/258,527 entitled "Diagnostic intraoral methods and apparatuses" filed Jan. 25, 2019.
Li et al.; U.S. Appl. No. 16/171,159 entitled "Alternative bite adjustment structures," filed Oct. 25, 2018.
Culp; U.S. Appl. No. 16/236,220 entitled "Laser cutting," filed Dec. 28, 2018.
Culp; U.S. Appl. No. 16/265,287 entitled "Laser cutting," filed Feb. 1, 2019.

* cited by examiner

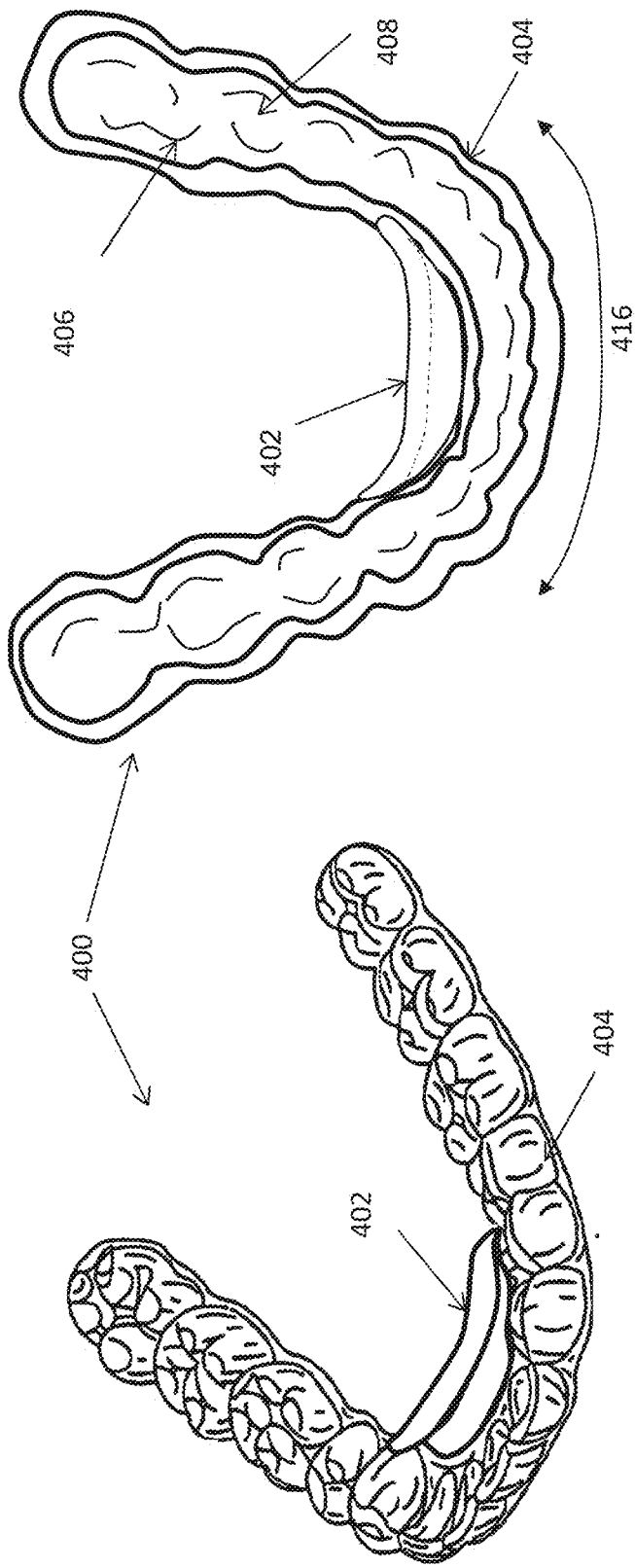
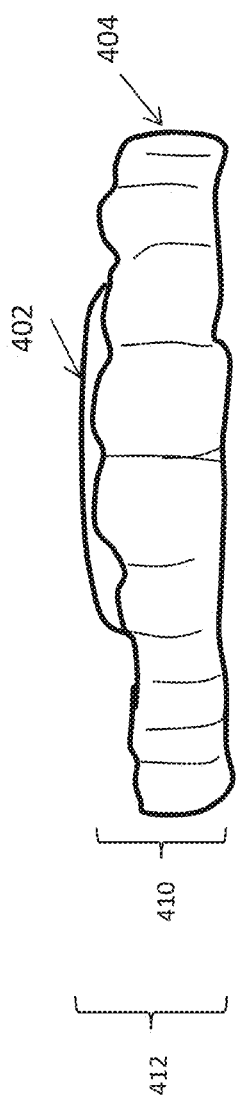
FIG. 4A
FIG. 4B
FIG. 4C

DENTAL APPLIANCE FEATURES FOR SPEECH ENHANCEMENT

CROSS REFERENCE TO RELATED APPLICATIONS

This application claims priority to U.S. Provisional Patent Application No. 62/429,548, titled "ALIGNER FEATURES FOR SPEECH ENHANCEMENT," filed on Dec. 2, 2016, and herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Current clear orthodontic aligners can open a patient's bite temporarily due to the thickness of the plastic trays. Because of the increased vertical dimension from the bite opening, the patient's tongue may not able to create an adequate anterior seal when certain sounds are spoken. A preferred vertical overlap of the anterior teeth is 2 to 4 mm, with less than 2 mm but greater than 0 mm being minimally acceptable. In particular, when the vertical overlap of the anterior teeth opens such that the tongue is unable to form a complete seal, the sibilants may be misarticulated, in some cases leading to lisping (or sigmatism). Inadequate vertical overlap of the posterior teeth (lateral open bite) can also contribute to a similar phenomenon stemming from the leakage of air due to an incomplete seal formed with the tongue. The inability to produce sibilant sounds properly during speech can be problematic for patients during work meetings, speaking over the phone, personal conversations, etc. As a result of this effect on speech, aligner wear compliance by the patient may be compromised, because the patients may simply leave out the aligners during work or during interactions with others in order to avoid lisping. If the amount of increased bite opening is relatively small, the tongue may adapt quickly over the course of a few weeks in order to create a better seal; however, compliance with aligner wear may be suboptimal until this time.

Some patients may naturally have a problem forming a seal between the tongue and the teeth even without a dental appliance in place, because of the presence of an anterior open bite, a lateral open bite, or both. The ability to reduce the open bite may improve the patient's speech, even if the open bite reduction is only temporary (i.e., while a dental device specifically designed for this purpose is being worn).

Described herein are orthodontic apparatuses (e.g., devices, appliances, etc.), including aligners and aligner features that may address these problems.

SUMMARY OF THE DISCLOSURE

The present application relates to an orthodontic device that may prevent, reduce, or inhibit poor speech articulation due to the inability to form an adequate seal between the tongue and the inner surfaces of a patient's teeth, which may result in lisping.

The devices may generally include an occlusal portion having a dentition-receiving cavity extending laterally in an arch and having a first vertical height, wherein the dentition-receiving cavity is configured to fit over a dental arch of a patient, the dentition-receiving cavity comprising an occlusal surface section adapted to be positioned over an occlusal surface of the patient's teeth. The device comprises a barrier portion extending laterally and adjacent to a region of the occlusal portion (e.g., a front region, a lateral region, etc.), the barrier portion having a second vertical height that is approximately the same height or a greater height than the first vertical height, wherein the barrier portion is laterally continuous to reduce or prevent air leakage therethrough, so that a patient's tongue may form a seal against the barrier portion when the patient is speaking while wearing the device.

In another aspect, the application relates to an orthodontic aligner device that prevents lisping. The device comprises an occlusal portion having a dentition-receiving cavity extending laterally in an arch and having a first vertical height, wherein the dentition-receiving cavity is configured to fit over a dental arch of a patient, the occlusal portion further configured to apply a force to a first set of teeth in the dentition-receiving cavity, the dentition-receiving cavity comprising an occlusal surface section adapted to be positioned over an occlusal surface of the patient's teeth; and a barrier portion extending laterally and adjacent to the occlusal portion, the barrier portion having a second vertical height that is greater than the first vertical height, wherein the barrier portion is laterally continuous to reduce or prevent air leakage therethrough, so that a patient's tongue may form a seal against the barrier portion when the patient is speaking while wearing the device.

In some embodiments, the barrier portion is positioned on a lingual side of the front region of the occlusal portion. The barrier portion can comprise a ridge. In some embodiments, the second vertical height of the barrier portion is more than about 0.5 mm higher than the first vertical height of the occlusal portion (e.g., greater than 0.8 mm, greater than 1 mm, between 1-6 mm, between 1-5 mm, between 1-4 mm, between 2-6 mm, between 2-5 mm, between 2-4 mm, etc.). In some embodiments, the second vertical height of the barrier portion is more than about 1 mm higher than the first vertical height of the occlusal portion. In some embodiments, the barrier portion is positioned on a buccal side of the front region of the occlusal portion. In some embodiments, the dentition-receiving cavity is configured to fit over an upper dental arch of the patient. In some embodiments, the dentition-receiving cavity is configured to fit over a lower dental arch of the patient. In some embodiments, the barrier portion is formed integrally with the occlusal portion. In some embodiments, the barrier portion is formed separately from and is attached to the occlusal portion. In some embodiments, the barrier portion is positioned lingual to the occlusal portion adjacent to a portion of the barrier portion that fits over a patient's incisors when the device is worn by the patient. In some embodiments, the barrier portion is positioned adjacent to a portion of the barrier portion that fits over a patient's incisors and canines when the device is worn by the patient. In some embodiments, the barrier extends posteriorly to create positive vertical overlap in the canine, bicuspid, and/or molar region. In some embodiments, the barrier is unilateral or asymmetric. In some embodiments, the barrier portion is curved and/or tapered. In some embodiments, the barrier portion is connected to or used in conjunction with bite ramp features used for temporary bite opening.

In another aspect, an orthodontic aligner device that prevents lisping is provided. The device comprises an aligner body having a dentition-receiving cavity extending laterally in an arch and having a first vertical height, wherein the dentition-receiving cavity is configured to fit over at least a portion of a dental arch of a patient, the aligner body further configured to apply a force to a first set of teeth in the dentition-receiving cavity, the dentition-receiving cavity comprising a plurality of upper surface sections configured to be positioned over occlusal surfaces of the patient's teeth when the device is worn over the dental arch of the patient, and a plurality of lateral wall surfaces configured to be placed in contact with sides of the patient's teeth when the device is worn over the dental arch, further comprising a first occlusal cut-out region at a first terminal end of the arch and a second occlusal cut-out region at a second terminal end of the arch, wherein the first cut-out region and the second cut-out regions are surrounded by lateral wall surfaces, with the occlusal surfaces of the patient's molars (and possibly also the premolars) exposed and able to touch the opposing arch when the device is worn over the teeth. This design may minimize the temporary anterior bite opening that can occur when orthodontic aligner appliances that cover the posterior teeth are being worn.

In some embodiments, the cut-out region extends over two or more teeth when the device is worn over the patient's dental arch. In some embodiments, the cut-out region extends over three or more teeth when the device is worn over the patient's dental arch. In some embodiments, a thickness of the occlusal surface of the device is thinner near the first and second terminal ends of the arch, and gets thicker towards a middle region between the first and second terminal ends of the arch. This middle region of the arch generally corresponds to the anterior teeth. In some embodiments, the cut-out regions extend into the lateral wall surfaces of the portion of the dentition-receiving cavity adjacent to the patient's molars when the device is worn over the dental arch. In some embodiments, the device comprises a barrier portion extending laterally adjacent to an anterior region of the aligner body, the barrier portion having a barrier vertical height that is greater than a first vertical height of the aligner body, wherein the barrier portion is laterally continuous to reduce or prevent air leakage therethrough, so that a patient's tongue may form a seal against the barrier portion when the patient is speaking while wearing the device.

In another aspect, a method of orthodontic treatment of a patient that prevents lisping is provided. The method comprises positioning an occlusal portion of an orthodontic device over the patient's dental arch so that the patient's teeth are contained within a dentition-receiving cavity of the occlusal portion, wherein, while the patient is wearing the orthodontic device, a barrier portion of the orthodontic device is positioned adjacent to a region of the occlusal portion and extends vertically beyond the occlusal portion and away from the patient's teeth, in order to provide a sealing surface for the patient's tongue during speaking.

In another aspect, another method to prevent lisping during orthodontic treatment of a patient is provided. The method comprises positioning an occlusal portion of an orthodontic device over the patient's dental arch so that the patient's teeth are contained within a dentition-receiving cavity of the occlusal portion which applies force to the patient's teeth to align the teeth by gradually moving the patient's teeth relative to each other when the orthodontic device is worn, wherein, while the patient is wearing the orthodontic device, a barrier portion of the orthodontic device that is positioned adjacent to a region (e.g., a front and/or lateral region) of the occlusal portion and extending vertically beyond the occlusal portion and away from the patient's teeth provides a sealing surface for the patient's tongue during speaking.

In some embodiments, the barrier portion extends laterally adjacent to the patient's incisors when the patient is wearing the orthodontic device. In some embodiments, the barrier portion extends in a continuous lateral surface adjacent to the patient's incisors when the patient is wearing the orthodontic device to reduce or prevent air leakage therethrough. In some embodiments, the method comprises differentially applying force to the patient's teeth to gradually move the patient's teeth relative to each other when the orthodontic device is worn. In some embodiments, the method comprises positioning a second occlusal portion of a second orthodontic device over a second dental arch of the patient so that the patient's teeth in the second dental arch are within a second dentition-receiving cavity of the second occlusal portion. In some embodiments, the method comprises positioning a second occlusal portion of a second orthodontic device over a second dental arch of the patient so that the patient's teeth in the second dental arch are within a second dentition-receiving cavity of the second occlusal portion and providing a second barrier portion of the second orthodontic device that is positioned adjacent to a second region of the second occlusal portion to provide a second sealing surface for the patient's tongue during speaking. In some embodiments, the lower jaw of the patient is able to reposition forward such that lower anterior teeth (with or without an orthodontic appliance) abut against a barrier portion located in the upper arch aligner in order to provide a sealing surface for the patient's tongue during speaking. In some embodiments, the lower jaw of the patient is able to rest against a vertical stop feature in the aligner such as a bite ramp feature, with a barrier portion located in the upper arch aligner built in to provide a sealing surface for the patient's tongue during speaking.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4A-4D illustrate embodiments of a device having a barrier portion.

In FIG. 12C the barrier portion extends laterally along the lingual side of the upper aligner, adjacent to and on either side of the bite ramp(s).

In FIG. 12D, the bite ramps (e.g., bite supporting structures) are integrated into the occlusal surface of the apparatus and a barrier region extends adjacent to the majority of the lingual side of the appliance to prevent air from escaping. The barrier region may have a height that is approximately the same or larger than the maximum height of the bite ramp(s). The dental appliance on the opposite side may be configured or otherwise adapted to allow the barrier region to seal any air leak between and/or over the occlusal surface(s) of the apparatuses. In FIG. 12E, the top view shows the barrier region is configured as a single barrier region extending from one side of the arch (adjacent to the rear molars) to the opposite side of the arch.

FIG. 13A shows an aligner with a tapered barrier portion in the upper aligner to provide a seal against lateral anterior air leakage when the upper bite ramps are engaged by the lower anterior dentition, especially when a deep Curve of Spee is present. FIG. 13C has an anterior barrier portion in the upper aligner to provide an anterior seal when anterior lingual bite ramps are engaged by the lower dentition.

In FIG. 18, the apparatus includes an upper and a lower orthodontic appliance; the barrier portion is on the upper appliance, however it may be positioned on the lower appliance. The upper and lower appliances in this example each include a pair of wings ("precision wings") that laterally interact with each other to engage with each other to reposition the patient's mandible (e.g., as part of a mandibular repositioning apparatus).

In FIG. 19A, the apparatus is one in a series of sequential palatal expanders that may be secured to the patient's upper arch through the dentition-receiving cavity formed on either side of the device; the dentition-receiving cavity includes a left dentition-receiving cavity portion and a right dentition-receiving cavity portion that are connected by a palatal region that is configured to be positioned adjacent to the patient's palate. Each device in the series of sequential expanders compresses in the transverse dimension enough during activation to engage the inner (lingual) surfaces of the posterior teeth, thereby transferring any expansion forces in the appliance through the posterior teeth to the palatal bone structures. In FIG. 19B, the apparatus of FIG. 19A is configured to include a front-facing (anterior) barrier region that may prevent lisping. The barrier region may be connected to an extension that extends from the palatal region.

DETAILED DESCRIPTION

Described herein are apparatuses including orthodontic devices that may prevent, reduce or inhibit sigmatism, or poor speech articulation of sibilants due to the inability of a patient's tongue to form a complete seal with the back of their teeth which results in lisping. Although the apparatuses and methods described herein are generally directed towards dental appliances, e.g., including, but not limited to aligners for treating teeth misalignment; any of these apparatuses and methods may be used for any other dental or orthodontic device, to improve speech when wearing such devices; furthermore, any of these apparatuses and methods may be used exclusively to treat existing patient miss-articulation (i.e., lisping). For example, these apparatuses may be configured as speech therapy devices. Examples of other appliances that may be configured or adapted to prevent speech problems and/or enhance comfort as described herein may include palatal expanders, mandibular advancement apparatuses, and the like. Any of the features shown herein for any specific appliance (e.g., aligners) may be used as par to any other dental appliance.

Figure 1:
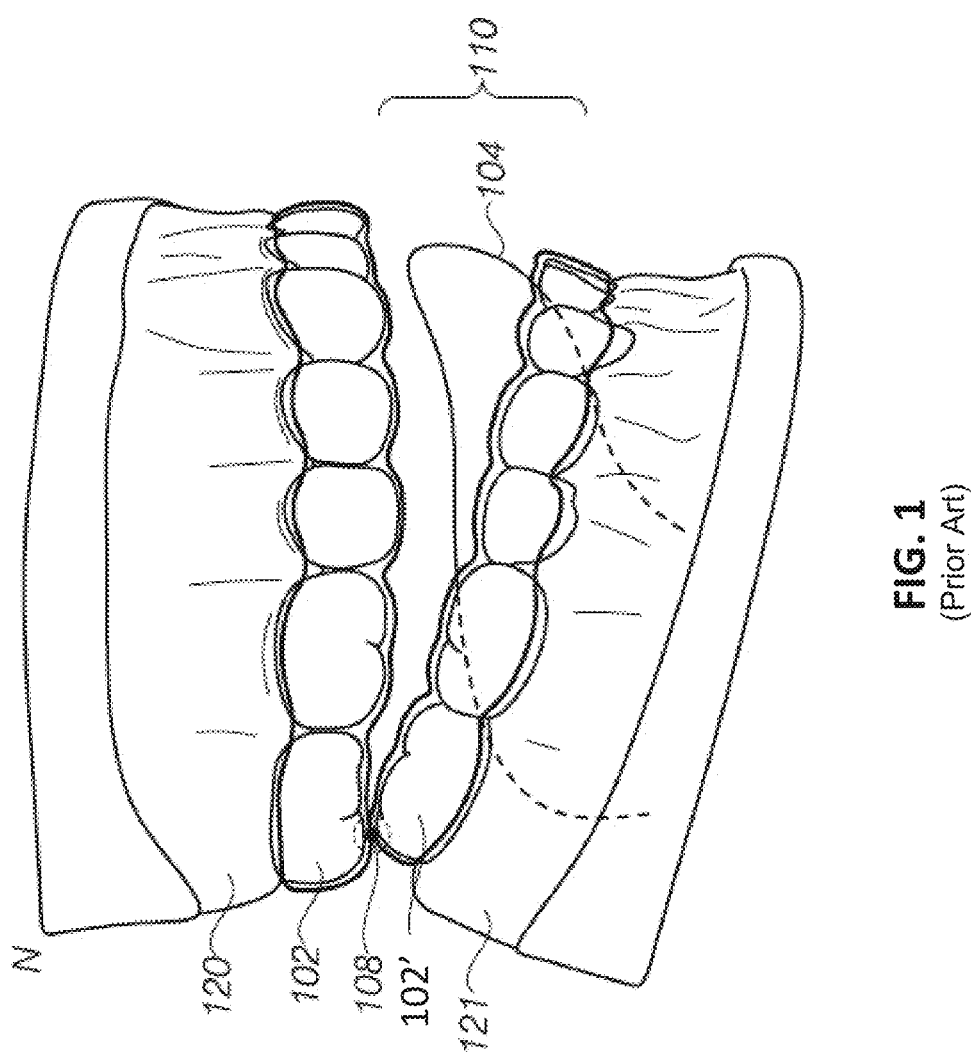
FIG. 1 illustrates a temporary bite opening effect by the use of aligners. There is a point of contact in the terminal regions of the arches due to the occlusal thickness of the aligners.

For example, disclosed herein are apparatuses and methods for addressing speech alterations caused by orthodontic appliances. FIG. 1 illustrates an example of an upper aligner 102 and a lower aligner 102'. An aligner, such as a shell type aligners shown in FIG. 1, can temporarily open the bite due to the thickness of the aligner on the occlusal surface of the teeth. In FIG. 1, a posterior contact 108 leads to an anterior opening 110. The opening 110 (which may be smaller than that illustrated in this example) can prevent the patient's tongue 104 from creating an adequate anterior seal when certain sounds are spoken, causing misarticulations. If patients are less likely to talk during the day or are less concerned about being embarrassed when speaking while wearing aligners, they are more likely to be compliant and wear the devices during their everyday social activities regardless of whether they lisp. If however, they need to talk without lisping or are embarrassed because they are lisping with the aligners in place, they are more likely to leave the aligners out during the day and only wear them when they are not interacting with others. This inconsistent usage may result in suboptimal orthodontic treatment results. Similar issues may occur with a single aligner or with other orthodontic appliances.

One way to address this problem is to reduce the thickness in the aligner which is increasing the vertical dimension and causing the bite to open. For example, thinning or removing portions of the aligner in the areas covering the posterior teeth (by creating occlusal windows, for example) can allow the back teeth to come closer together (or touch) in order to let the front portions come closer together, thereby reducing the impact of increasing the vertical dimension. For patients with a high a mandibular plane angle, any increase in the vertical dimension of the posterior teeth results in a magnified increase in the anterior vertical dimension. In other words, the change in the anterior is not necessarily 1:1 with the vertical change in the posterior, and may be a multiple instead (e.g., 2× or 3×).

Figure 2B:
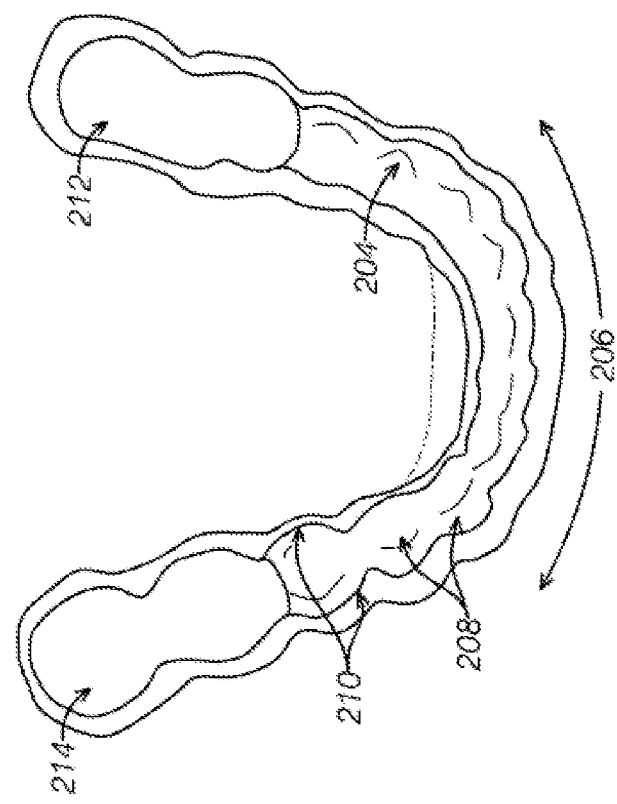
FIGS. 2A and 2B illustrate an embodiment of an aligner having occlusal windows in the terminal regions of the arch. The portions covering the molars have been removed.
Figure 2A:
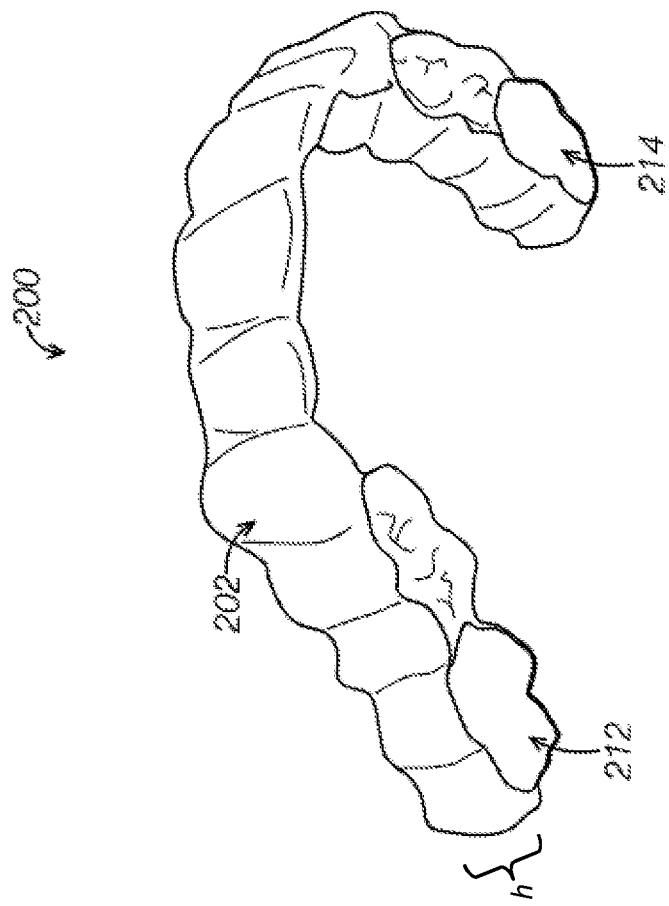

FIGS. 2A and 2B illustrate an embodiment of a device having occlusal windows. FIG. 2A illustrates a perspective view of an aligner 200 comprising an aligner body 202. As shown in the bottom view of FIG. 2B, the aligner body 202 has a dentition-receiving cavity 204 extending laterally in an arch, as shown by arrow 206 and having a first vertical height, h. The dentition-receiving cavity 204 is configured to fit over at least a portion of the dental arch. The aligner body 202 may be configured to apply a force to a first set of teeth in the dentition-receiving cavity 204. The dentition-receiving cavity 204 comprises a plurality of upper surface sections 208 configured to be positioned over the occlusal surfaces of the patient's teeth when the device is worn over the dental arch of the patient. These sections may divide the body region 202 into a plurality of (in this example, laterally contiguous) chambers each substantially conforming to individual teeth. In some variations the dentition-receiving cavity may be separate sub-regions (e.g., on either side of the arch). Alternatively or in addition, the dentition receiving cavity may include a gap or space where a tooth is missing; in some variations the body 202 is configured to attach to just a portion of the patient's dental arch (e.g., the molar/pre-molar region, etc.). The dentition-receiving cavity 204 may comprise a plurality of lateral wall surfaces 210 configured to be placed in contact with surfaces of the patient's teeth when the device is worn over the dental arch. The dentition-receiving cavity 204 in this example includes a first cut-out region 212 at a first terminal end of the arch and a second cut-out region at a second terminal end (e.g., posterior ends) of the arch. The first and second cut-out regions are surrounded by lateral wall surfaces and expose the occlusal surfaces of the patient's molars when the device is worn over the dental arch. The occlusal window can extend over two or more teeth (e.g., all the molars) or three or more teeth. In some embodiments, a thickness of the occlusal surface sections is thinner near the first and second terminal ends of the arch and becomes thicker towards the anterior region of the arch. The cut-out regions or windows can extend into the lateral wall surfaces of the portion of the dentition-receiving cavity adjacent to the patient's molars.

Figure 3A:
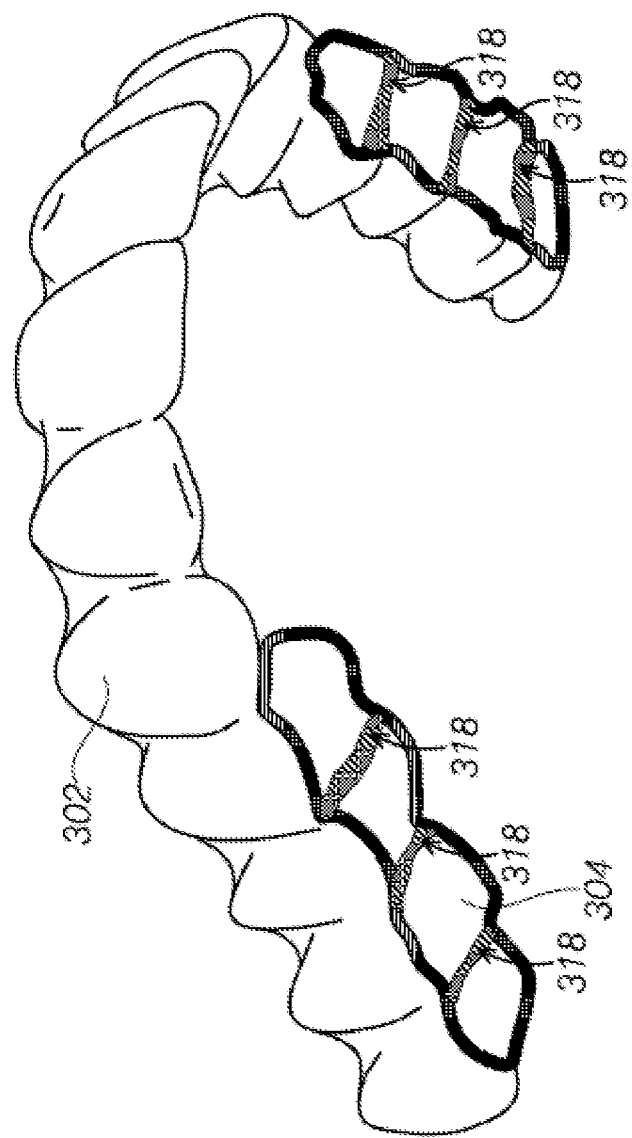
FIGS. 3A and 3B illustrate additional embodiments of aligners having occlusal windows. Portions of the aligner (on the occlusal surfaces) over both the molars and the premolars have been removed. Some occlusal regions in between the teeth have not been removed in order to provide crossbeam-like structural supports between the buccal and lingual walls of the plastic appliance (interproximal cross supports).
Figure 3B:
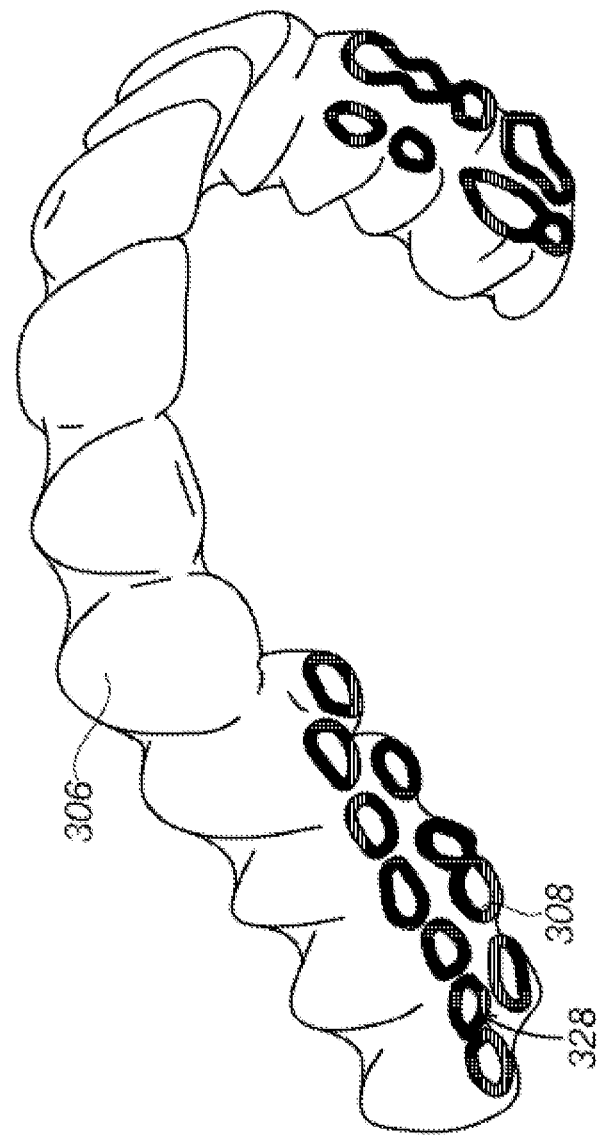

FIGS. 3A and 3B show additional embodiments of an aligner comprising occlusal windows or cutouts. As shown in FIG. 3A, the cutouts include interproximal supports 318 between buccal and lingual surfaces. The aligner 302 comprises occlusal windows 304 or cut-outs over the occlusal surfaces of the back 4 teeth on each terminal end of the arch. In some embodiments, the occlusal window can be positioned over 1, 2, 3, 5, 6, or more teeth of the dental arch. The occlusal window can be positioned at a terminal end of the dental arch. In some embodiments, the occlusal window is spaced away from a terminal end of the dental arch. The aligner can comprise 1, 2, 3, 4, or more occlusal windows positioned along the aligner body.

In some cases, removal of too much of the occlusal portion can reduce rigidity of the aligner. Thus, in some variations, only the cusp tips or occlusal portions may be removed, leaving the interproximal cross supports 328 in place, as shown in FIG. 3B. Alternatively or additionally, these cross supports may be reinforced.

An additional and/or alternative solution may include a barrier (barrier region) in the anterior (and in some variations lateral) portion(s) of the aligner that provides a similar or decreased vertical dimension to what the patient had prior to wearing the aligners, so that the tongue is able to form a similar or better anterior seal while the aligners are being worn. In this manner, the problem of the lisp is reduced or eliminated and patients may be more likely to wear the aligners during the day and during social settings.

In some embodiments, for small increases in vertical dimension, the feature may not be needed, but for patients with shallow overbite, open bite, patients with Class II or Class III overjet, or patients with occlusal features in the aligner that prevent them from closing down into maximum intercuspation, the need for an anterior seal becomes greater.

The anterior seal can be facilitated by providing a barrier that helps the tongue reduce or prevent air leakage so that lisping during speech is reduced or eliminated. This barrier can comprise a protrusion that spans in the mesial-distal direction along the arch, across several teeth and positioned either on the buccal or lingual of the teeth, depending on the arch. This feature may also be used in the posterior portion of the aligner for patients with lateral open bites, where air leakage during speech occurs in the lateral or posterior-lateral regions of the arch. If the air leakage is occurring laterally (e.g., near the canines and premolars), the desired outcome may be accomplished with a barrier which creates a lateral seal with the tongue.

Figure 4D:
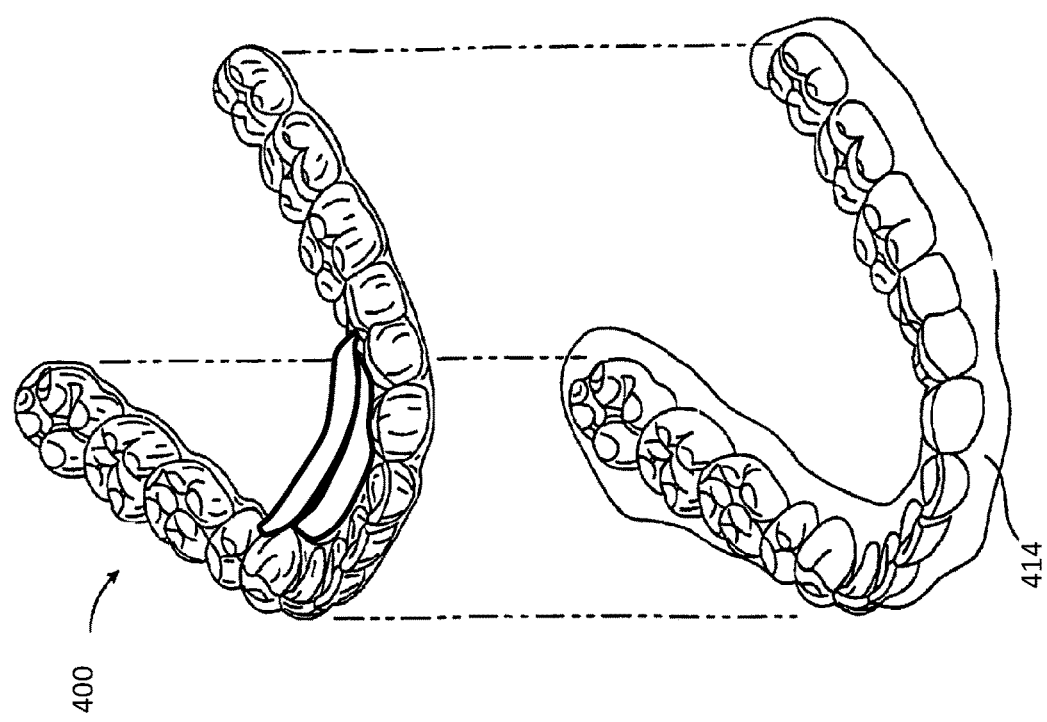

FIGS. 4A-D illustrate an embodiment of an orthodontic appliance (in this example, an aligner) 400 comprising a barrier portion 402. As shown in the top perspective view of FIG. 4A and the bottom view of FIG. 4B, the aligner comprises an occlusal portion 404 having a dentition-receiving cavity 406 extending laterally in an arch as shown by arrow 416. The occlusal portion has a first vertical height 410, as shown in the front view of FIG. 4C. The dentition-receiving cavity 404 is configured to fit over a dental arch of a patient. The dentition-receiving cavity comprises an occlusal surface section 408 adapted to be positioned over an occlusal surface of the patient's teeth. The aligner 400 also comprises a barrier portion 402 extending laterally and adjacent to a region of the occlusal portion 404. The barrier portion has a second vertical height 412 that may be at approximately the same or greater height (e.g., 0.5 mm greater, 1 mm greater) than the first vertical height 410. The barrier portion is laterally continuous to reduce or prevent air leakage there through, so that a patient's tongue may form a seal against the barrier portion when the patient is speaking while wearing the device. FIG. 4D shows the aligner 400 fitting over a patient's dental arch 414. In any of these variations the height of the barrier region may be approximately 1× or greater (e.g., 1.01×, 1.02×, 1.03×, 1.04×, 1.05×, 1.1×, 1.15×, 1.2×, 1.25×, 1.3×, 1.35×, 1.4×, 1.45×, 1.5×, etc. or greater) the height of the maximum vertical height of the appliance. The barrier region may have any lateral extent, and may typically extend along the distal (anterior) region (e.g., adjacent to the anterior teeth). For example, the barrier region may extend adjacent to the entire dental arch (e.g., adjacent to the incisors, from canine to canine, from premolar to premolar, from molar to molar, etc.).

Figure 5:
FIG. 5 illustrates an example of a tongue crib appliance 501 which is typically used to prevent the tongue from pushing the anterior teeth forward.

A side benefit of the barrier feature is that orthodontic forces on the teeth which come from the tongue pushing out the teeth bucally/facially may be reduced. The barrier feature may employ the same principle as a "tongue crib" (see, e.g., FIG. 5) for tongue thrust correction; but, unlike a tongue crib 501 which is open and made of wire, the feature claimed is continuous laterally to reduce or restrict the air flow, and allow seal to be made, which may be helpful for speech articulation. If mild air flow is desired for improved salivary circulation or improved air circulation during breathing, perforations or other surface alterations like channels or ridges may be added to the feature. Here, any perforations need to be small enough so as not to disrupt the primary objective of creating an adequate barrier seal with the tongue during speaking in order to avoid lisping.

The following figures depict various embodiments of appliances with barrier features. Unless described otherwise, the appliances described below may comprise occlusal portions and dentition-receiving cavities as described with respect to FIGS. 4A-4D, above. Furthermore, a 'front portion' of an occlusal portion with a dentition-receiving cavity fitting over the dental arch may refer to the area near the canines and incisors, but may refer to a smaller (e.g., not extending past the incisors) or greater (e.g., extending past the canines) region than that. The 'front portion' of an occlusal portion with a dentition-receiving cavity fitting over the dental arch may refer to the area near the front 2-4 teeth, 2-6 teeth, or 2-8 teeth.

Figure 6:
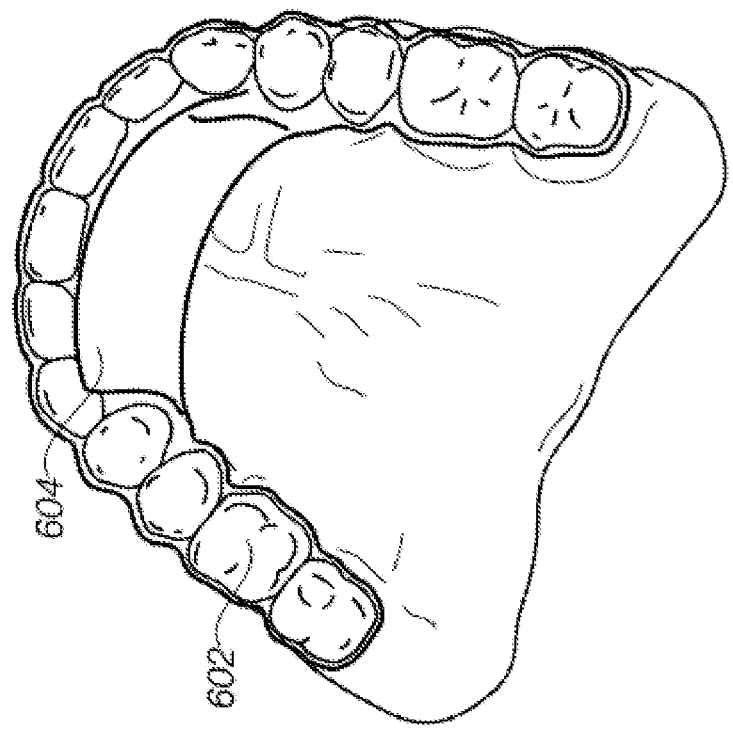
FIG. 6 schematically illustrates an embodiment of an upper aligner having a barrier feature.

FIG. 6 illustrates a bottom view of an embodiment of an upper aligner comprising a barrier feature 604 positioned proximate to a front portion of an occlusal portion 602 of the aligner. The barrier feature 604 comprises a continuous ridge in the aligner for the purpose of creating an anterior seal with the tongue in order to reduce or prevent air leakage during speaking.

Figure 7:
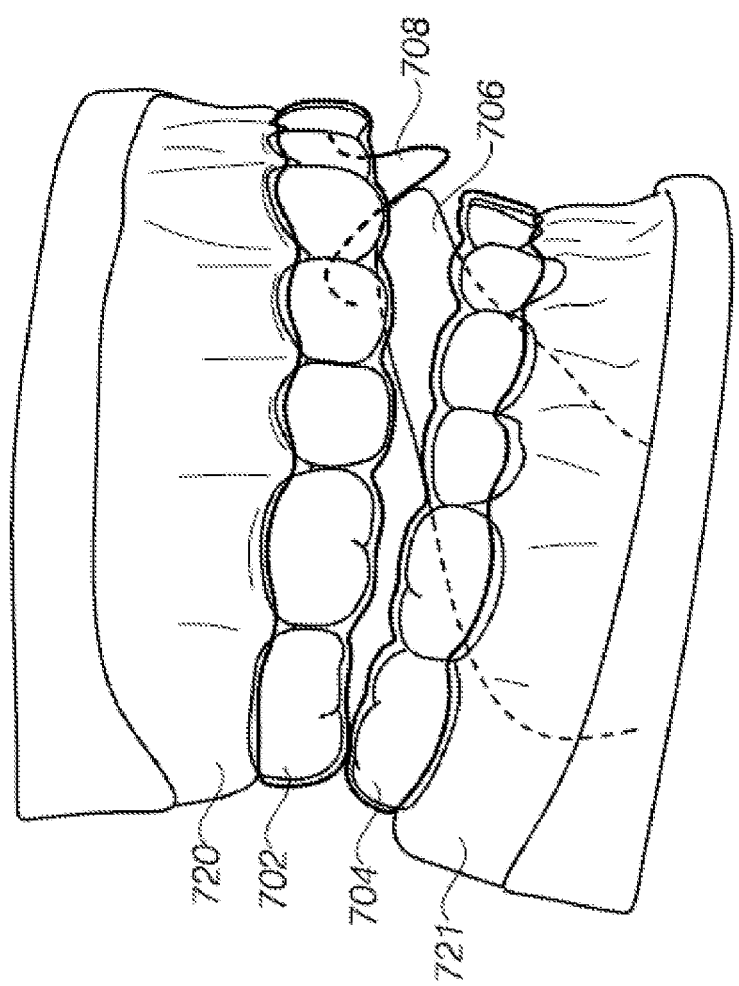
FIG. 7 illustrates embodiments of upper and lower aligners, the upper aligner having a barrier portion. The lower aligner may come into close proximity of the upper aligner in the patient's existing bite relationship, or after the patient repositions the lower jaw forward. This configuration may be useful if a patient has an excessive overjet which leads to a large anterior opening.
Figure 17B:
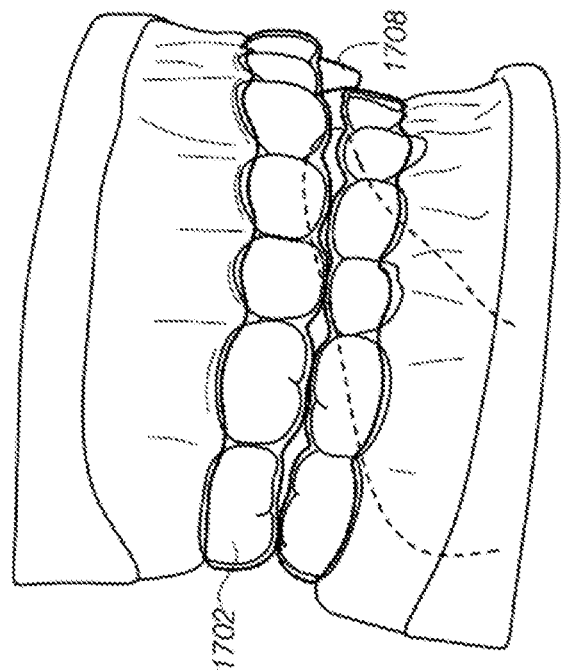
FIGS. 17A and 17B illustrate an upper aligners having a barrier portion similar to that shown in FIG. 7, in which the lower jaw (which may or may not have an aligner) may slide forward to a forward-repositioned location (shown in FIG. 17B) whereby a reduced anterior gap is created between the upper barrier and the lower teeth.
Figure 17A:
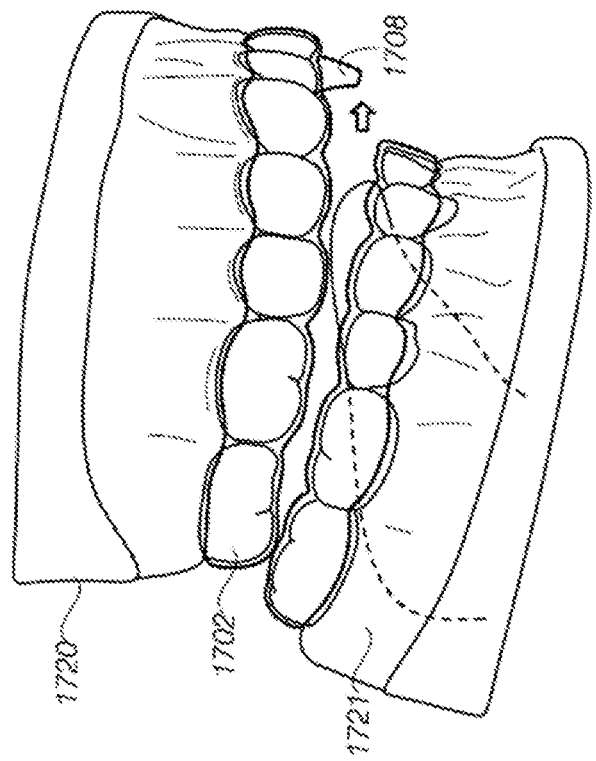

FIG. 7 illustrates a side view cross-section of an embodiment of an aligner comprising an upper aligner 702 and lower aligner 704, wherein the upper aligner comprises a barrier portion 708 and being worn by a patient. The upper aligner is shown on a model of the upper jaw teeth 720; the lower aligner is shown on a model of the lower jaw teeth 721. The barrier portion 708 is positioned proximate to a front portion of the upper occlusal portion. The barrier portion 708 comprises a mesial-distal barrier, in this embodiment positioned lingual to the dentition, which creates a barrier with the lower anterior teeth so that air leakage is reduced or eliminated when the patient speaks. FIG. 7 depicts the tongue 706 encountering the barrier portion 708. While FIG. 7 shows a lingual positioning for the barrier portion 708, buccal positioning is also possible. As mentioned above, the lower jaw of the patient may be able to reposition forward such that lower anterior teeth (with or without an orthodontic appliance) abut against a barrier portion located in the upper arch aligner in order to provide a sealing surface for the patient's tongue during speaking. This is illustrated, for example, in FIGS. 17A and 17B. In this example, similar to that shown in FIG. 7, an upper aligner 1702 includes a barrier portion 1708 lingual to the upper anterior teeth and is shown on the upper jaw 1720. The lower jaw 1721 sliding forward into a forward-repositioned location whereby a reduced anterior gap is created between the upper barrier 1708 and the lower teeth 1721.

Figure 8:
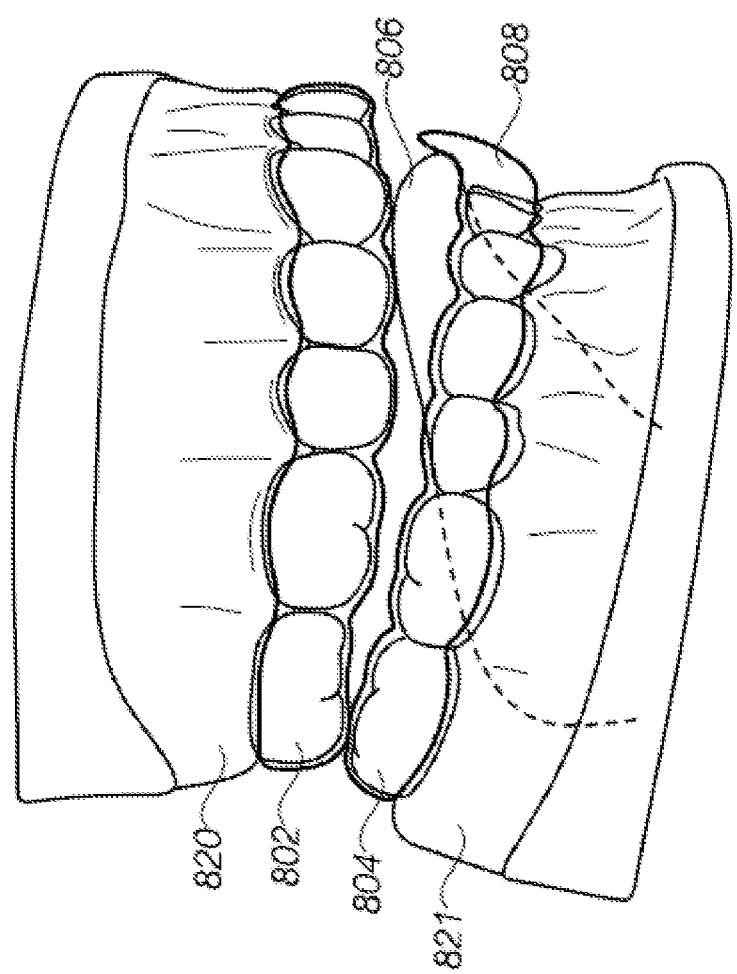
FIG. 8 illustrates embodiments of upper and lower aligners, the lower aligner having a barrier portion. This configuration may be useful if a patient has an excessive overjet which leads to a large anterior opening.

FIG. 8 illustrates a side view cross-section of an embodiment of an aligner comprising an upper aligner 802 and a lower aligner 804, the lower aligner 804 comprising a barrier portion 808. The upper aligner is shown on a model of the upper jaw teeth 820; the lower aligner is shown on a model of the lower jaw teeth 821. The barrier portion 808 is positioned near a front portion of an occlusal portion of the lower aligner 804 (a proximate or adjacent to the portion covering the canines and/or incisors). The barrier portion 808 comprises a mesial-distal barrier along the arch positioned near or on the dentition, which creates a barrier with the upper anterior teeth so that air leakage is reduced or eliminated when the patient speaks. FIG. 8 shows the tongue 806 encountering the barrier portion 808. The barrier portion 808 may typically be positioned lingually in the upper arch, particularly for patients with excessive overjet, but buccal positioning in the lower arch is also contemplated as shown in FIG. 8. In some embodiments, a lower barrier portion 808 may be useful if an upper barrier portion is less desirable (e.g., aesthetically undesirable).

Figure 9:
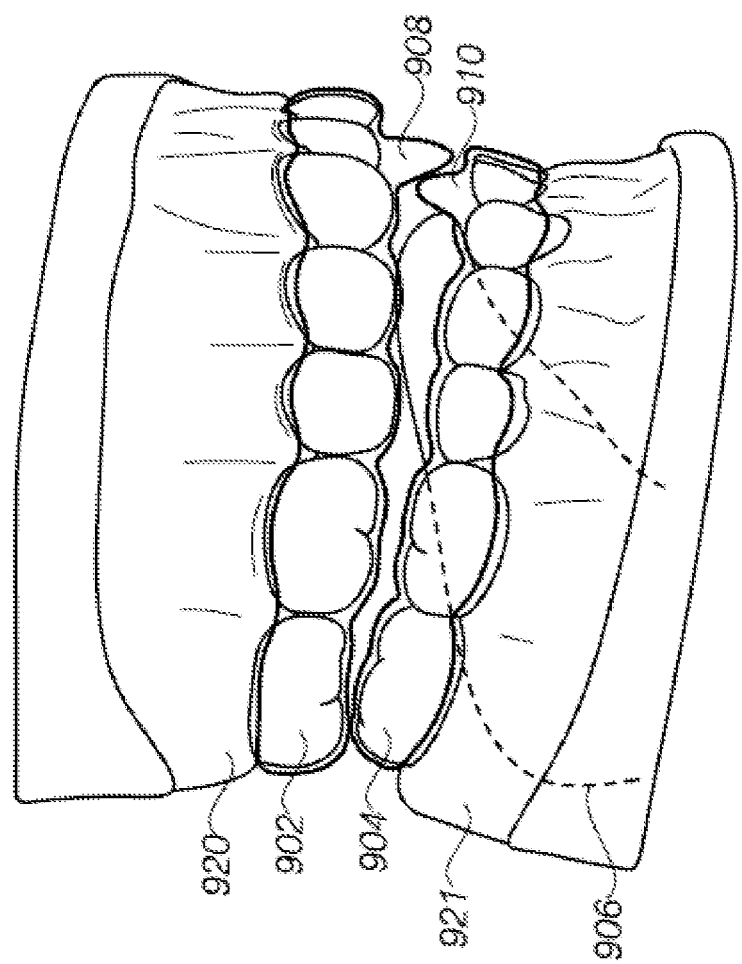
FIG. 9 illustrates embodiments of upper and lower aligners both having barrier portions. The barrier positions may come into close proximity in the patient's existing bite relationship, or after the patient repositions the lower jaw forward. This configuration may be necessary if a patient has an excessive overjet which leads to a large anterior opening, and/or if a patient has an anterior open bite which cannot be sealed by only one barrier alone.

FIG. 9 illustrates an embodiment of an upper aligner 902 comprising an upper barrier portion 908 and a lower aligner 904 comprising a lower barrier portion 910. The upper aligner is shown on a model of the upper jaw teeth 920; the lower aligner is shown on a model of the lower jaw teeth 921. One barrier in each arch may be needed if the anterior vertical dimension is excessive (in severe anterior open bite patients, for example) whereby the barrier height needed is greater than what is practical or possible to manufacture into a single aligner. The barrier portions 908, 904 may be positioned towards a front portion of their respective occlusal portions. In some embodiments, one or both of the barrier portions are positioned away from the front portion of their respective occlusal portions. Both of the barrier portions 908, 910 may be positioned lingually. In some embodiments, one barrier portion can be positioned lingually and the other buccally. In some embodiments, both barrier portions are positioned buccally, but for esthetic reasons, typically this configuration would more likely be used in the case of patients with lateral open bites. FIG. 9 shows the tongue 906 encountering the barriers 908, 910.

Figure 10:
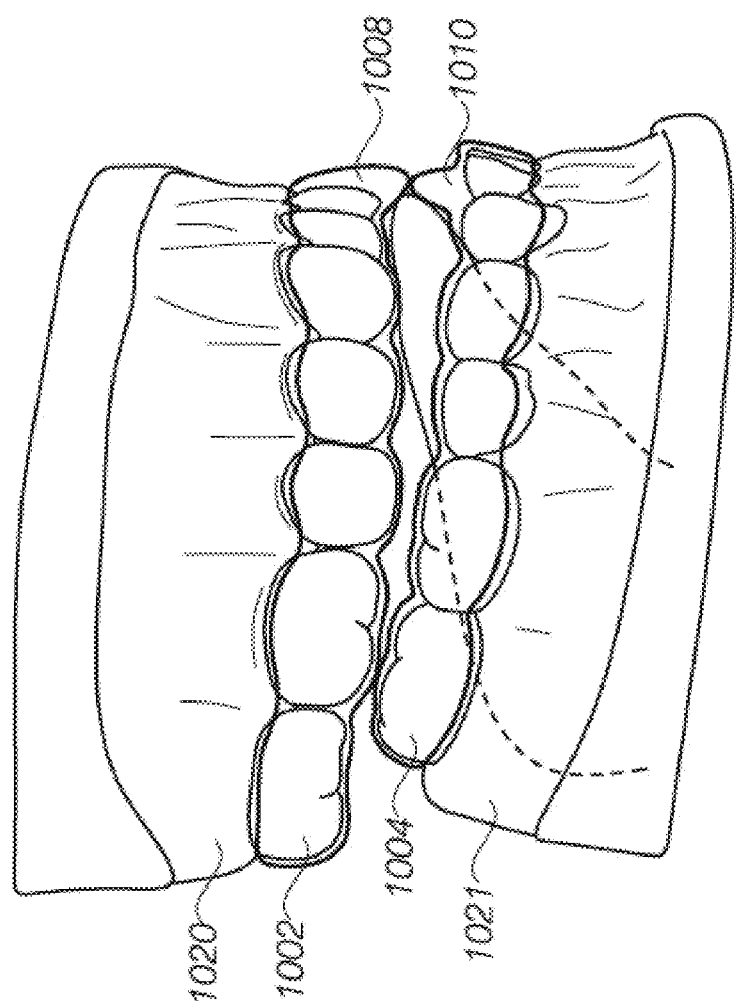
FIG. 10 illustrates embodiments of upper and lower aligners having barrier portions. This configuration may be useful if a patient has a negative overjet which leads to a large anterior opening.

In some embodiments, the barrier feature is lingually positioned on the lower arch of the aligner or buccally located on the upper arch of the aligner. Such embodiments may be appropriate for patients with Class 3 bite relationships, in which the lower arch is forward of the upper jaw position in a negative overjet relationship. FIG. 10 depicts an embodiment of an upper aligner 1002 with an upper barrier portion 1008 and a lower aligner 1004 with a lower barrier portion 1010. The barrier portions 1008, 1010 are positioned proximate or adjacent to a front portion of their respective aligner's occlusal portion. The upper barrier portion 1008 is positioned buccally, and the lower barrier portion 1010 is positioned lingually. This configuration may not be esthetically feasible in the upper arch, so having the feature present only in the lower arch may be required for Class 3 patients with significant negative overjet. The upper aligner is shown on a model of the upper jaw teeth 1020; the lower aligner is shown on a model of the lower jaw teeth 1021.

Figure 11:
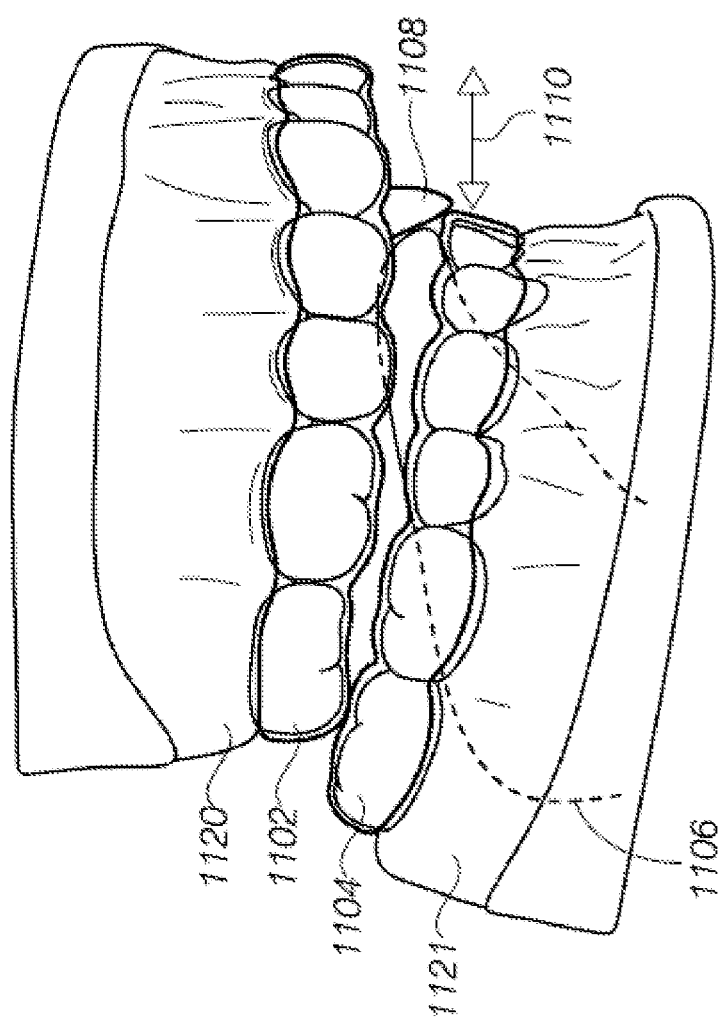
FIG. 11 illustrates embodiments of an upper and lower aligner, the upper aligner having a barrier portion. This configuration may be useful if a patient has an excessive overjet which leads to a large anterior opening, particularly if the patient is unable to sufficiently advance the lower jaw forward to create an adequate anterior seal with the tongue.

FIG. 11 shows an embodiment of an upper aligner 1102 and a lower aligner 1104, the upper aligner 1102 comprising a barrier portion 1108. The barrier portion 1108 is positioned toward the front of an occlusal portion of the upper aligner 1102 and is positioned lingually or closer to the palatal region. Such an embodiment can be appropriate for Class 2 patients with excessive overjet 1110, particularly if the patient's lower jaw is no longer growing or if the jaw is unable to reposition forward into a stable Class 1 bite relationship. The barrier portion may be positioned closer to or even on the palatal region. FIG. 11 shows the tongue 1106 encountering the barrier portion 1108. The upper aligner is shown on a model of the upper jaw teeth 1120; the lower aligner is shown on a model of the lower jaw teeth 1121.

Figure 12A:
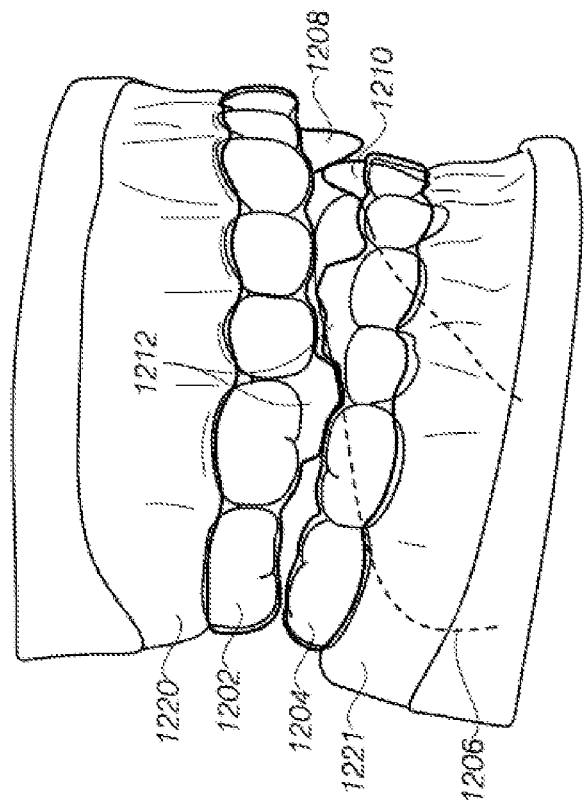
FIGS. 12A and 12B illustrates embodiments of upper and lower aligners with jaw repositioning features in the upper and lower arches and also having a barrier portion in the upper aligner (FIG. 12A) or in both the upper and lower aligners (FIG. 12B).
Figure 12B:
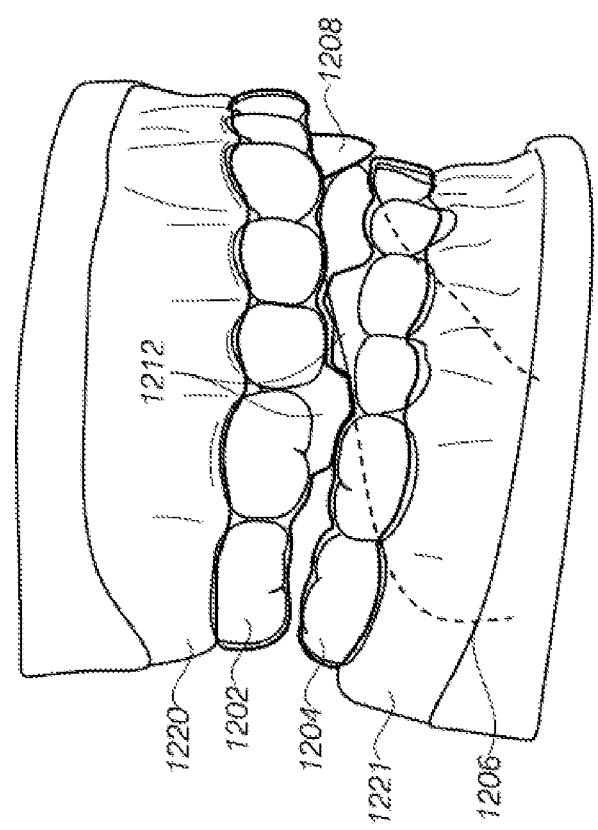

Some embodiments of aligners comprise aligner features which open the patient's bite. In such embodiments, an anterior seal may become even more critical, because of the temporary anterior open bite intentionally created when the aligners are worn. FIGS. 12A and 12B depict embodiments of an upper aligner 1202 having an upper barrier portion 1208, and in FIG. 12B and upper 1208 and a lower aligner 1204 having a lower barrier portion 1210. The aligners comprise bite repositioning features 1212 (e.g., twin block features). FIGS. 12A and 12B, respectively, show the tongue 1206 encountering the barrier portions 1208, 1210. The upper aligner is shown on a model of the upper jaw teeth 1220; the lower aligner is shown on a model of the lower jaw teeth 1221.

Figure 12C:
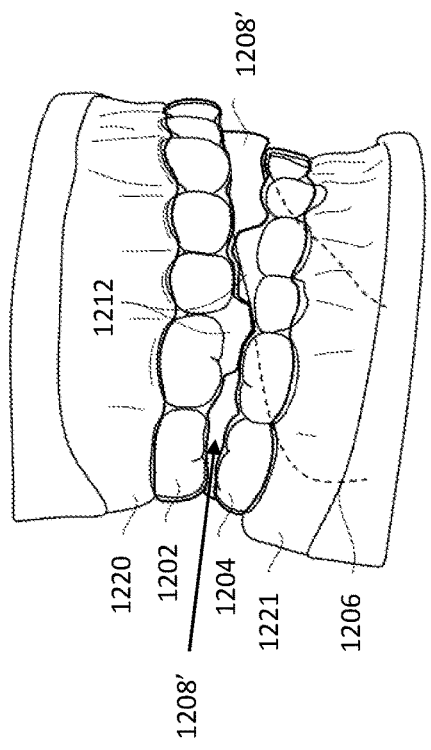
FIG. 12C is another example of a pair of upper and lower jaw appliances including bite ramps and a barrier portion to enhance speech and/or patient comfort.

As mentioned above, any of the apparatuses (e.g., appliances, including but not limited to aligners) described herein may include a barrier region (or multiple barrier regions) that extend laterally along the side, e.g., adjacent to the premolars and/or molars. These apparatuses may therefore prevent air leakage from the sides and/or allow sealing by the tongue along these lateral side regions. In apparatuses, such as the example shown in FIG. 12A-12B, that may induce or address a lateral open bite, a lateral lingual or buccal barrier may be include to reduce or prevent leakage. For example, in FIGS. 12C to 12E the barrier region extend adjacent to the majority of the apparatus. For example, in FIG. 12C the apparatus includes an upper appliance 1202 and a lower appliance 1204 similar to those shown in FIG. 12A-12B. In FIG. 12C, the barrier portion 1208' is not limited to the anterior portion, but extends long both sides of the appliance (e.g., the upper and/or lower appliance). This may prevent air leakage from the sides of the appliance(s). Any of these apparatuses may be included along with an occlusal stop so that there is a resting position in which the appliance sits on the back teeth (e.g. molars).

Figure 12E:
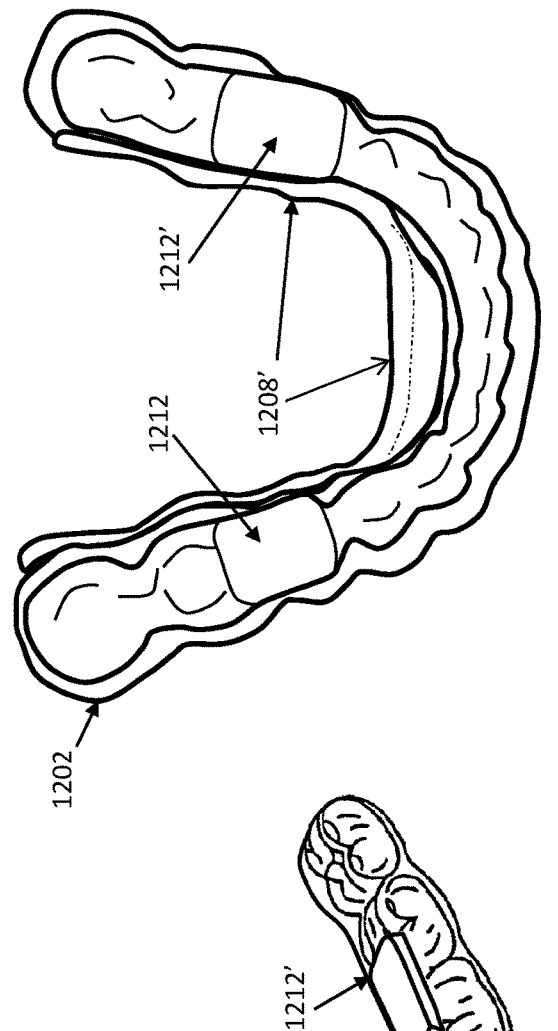
FIGS. 12D and 12E illustrate front perspective and top bottom views, respectively, of the upper jaw appliance (which may be configured as an aligner).
Figure 12D:
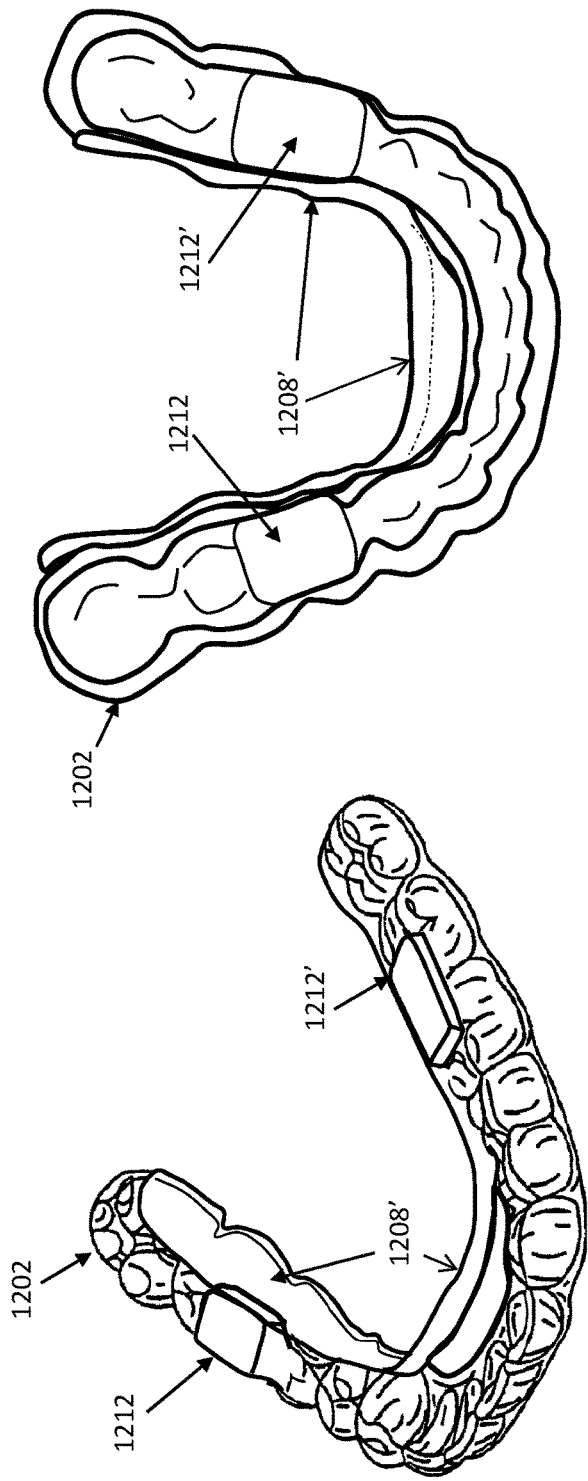

In FIG. 12C, as shown in FIG. 12A-12B, the bite repositioning features 1212 on the upper and lower appliances may limit the closure (intercuspation) of the teeth on the upper and lower arches; in any such variations in which the bite is modified, a barrier region may be included. FIG. 12D, for example, illustrates an example in which a barrier region 1208' extends lateral from the right rear molar to the left rear molar along the entire lingual side, and adjacent to the bite repositioners 1212, 1212'. The height of the barrier region is typically the same or larger than the maximum height of these bite repositioners; the height of the barrier region may vary along the length. The barrier region may be positioned laterally on the lingual side (as shown in FIGS. 12D and 12E) or on the buccal side. The barrier may act as a shield, for example (e.g., a lingual shield), preventing the tongue from interacting with the spacer(s) and/or the appliance. In FIG. 12E, the top view shows the appliance in which the barrier region 1208' is recessed slightly lingually from the appliance.

Figure 13A:
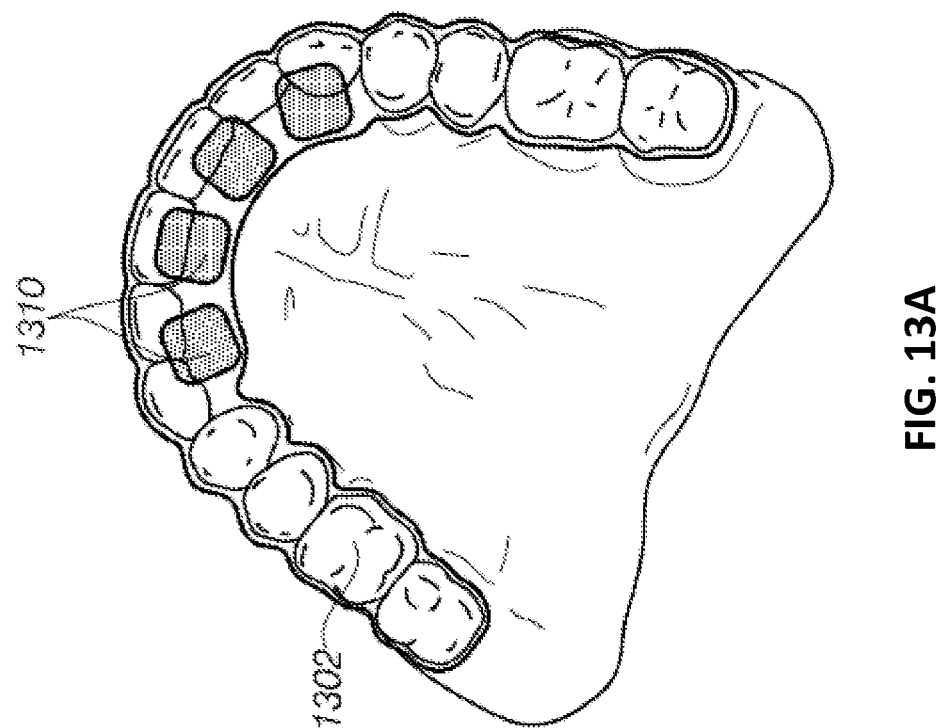
FIGS. 13A-13C illustrates embodiments of aligners having anterior bite ramps.
Figure 13C:
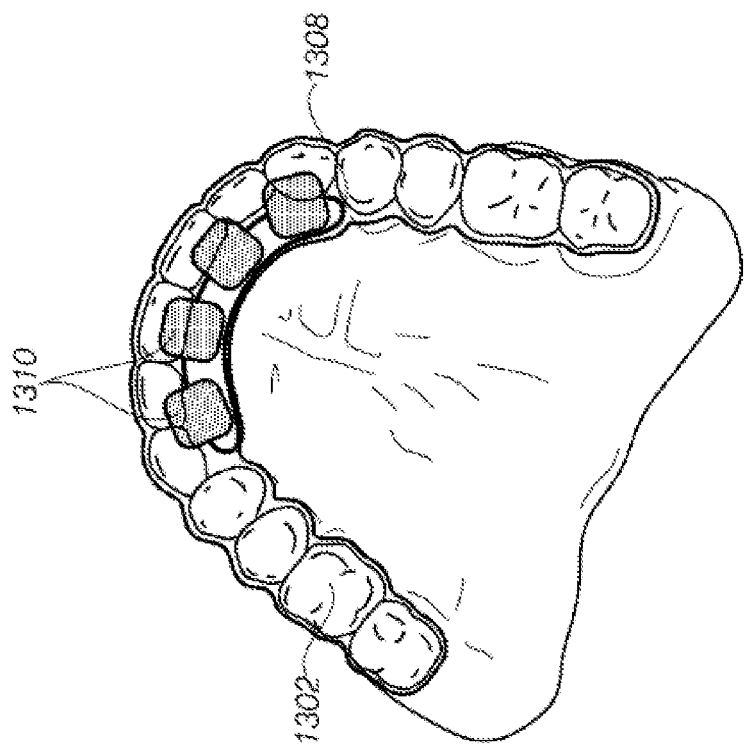
Figure 13B:
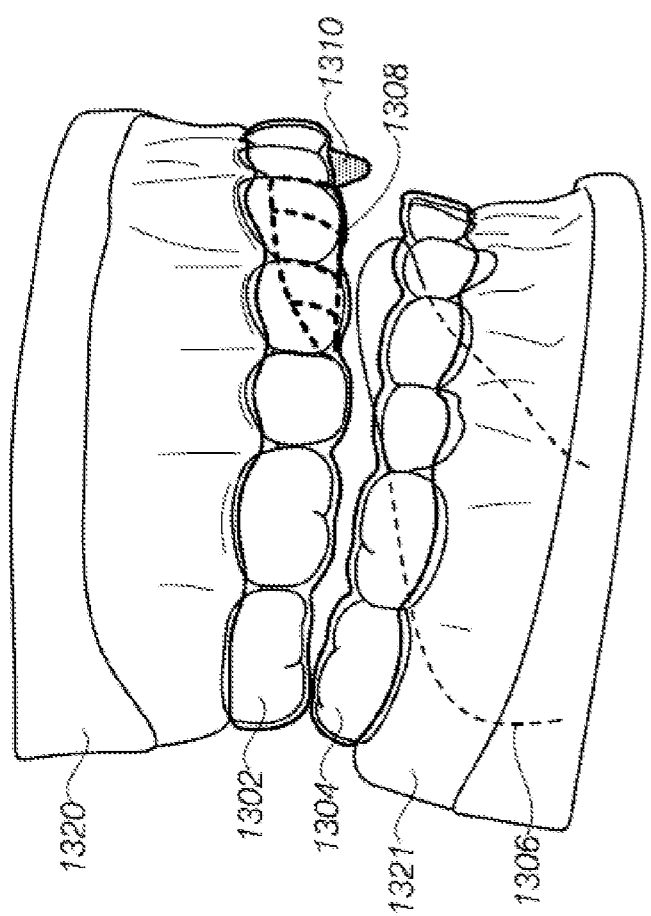

Barrier portions can also be advantageous in embodiments of aligners 1302 in which anterior bite ramps 1310 are used in the upper lingual area, as shown in FIG. 13A. In such embodiments, the addition of a barrier can be desirable in order to form a seal with the tongue and reduce or prevent air leakage. Anterior bite ramps are often used when treating patients with a deep bite and an accentuated curve of Spee, and this curve often leads to a lateral opening prone to air leakage when the lower jaw is advanced forward. FIG. 13B illustrates embodiments of an upper aligner 1302 and a lower aligner 1304. FIG. 13B shows a side view of both aligners in the mouth (shown on a partial sectional view of a patient's mouth or a model of a patient's upper and lower jaws, for simplicity). In FIG. 13B, the barrier 1308 is in front of the bite ramp 1310. The lower jaw 1321 may slide forward (anteriorly) and rest on the anterior vertical stops (bite ramps 1308) which may also contain a barrier portion to block air leakage. FIG. 13C shows a bottom view of the upper aligner 1302. The upper aligner 1302 comprises bite ramps 1310 and a barrier portion 1308.

When implementing the treatments described herein, customized aligners can be used. A simulation of an aligner including features can be placed over the thickness of the teeth. The simulated aligner can include any features used by the patient, such as bite ramps or bite repositioners. The effect of the aligner on the bite is observed in the simulation. Virtual, digital modeling can show the bite angle changes using, for example, a virtual articulator, which can, in turn, show how much the bite opening changes the vertical dimension. Based on such a simulation, a barrier feature can be created to return the bite to a normal vertical dimension.

Generally, the goal is for the barrier portion to extend vertically and create an artificial overbite. In some embodiments, the barrier portion may have to expand beyond the perimeter of the arch. The patient's facial shape may influence the configuration of the barrier portion. Jaw angle can correspond to face shape. For example, a long facial profile (i.e., dolichofacial) can comprise a downward sloping angle in the lower jaw, while a short, square face pattern (i.e., brachyfacial) can comprise a more parallel angle between the lower and upper jaws. In patients with the long facial pattern, the downward sloping angle of the mandible can exaggerate any opening caused by a thickness on the occlusal surfaces of the back teeth. In such cases, the barrier portion can utilize a tapering height to avoid adding any thickness to the aligners in the posterior regions near the terminal ends. For example, the barrier extension can be 3 mm vertical in the front, but taper to 0 mm in height closer towards the back teeth of the dental arch.

A patient may receive an orthodontic treatment course with a series of aligners, for example 20-40 aligners. New sets of aligners can be provided to the patient by the doctor every few weeks. Each aligner is configured to provide orthodontic forces which gradually move the teeth. The barrier portions may be provided in a first subset (e.g., the first 5-10 aligners) of the series, and not be provided in the aligners to be used later.

The barrier portion can be manufactured as part of the aligner, similar to aligner ridges and bite ramps. Alternatively, the barrier portion can be a piece that is manufactured separately (e.g. 3-D printed, milled, or injection molded) and then connected to the aligner in a separate manufacturing step (with adhesive, spot welding, ultrasonic welding, etc.). Alternatively, the barrier portion can be 3-D printed in a different material in the case of 3-D printed aligner appliances. This avoids needing a separate manufacturing step to connect the barrier portion to the aligner appliance.

When a barrier is included as part of aligner in a series of aligners, the position and/or size of the barrier may change within the series. For example, the initial aligners in the series may include a barrier (or a larger barrier); the barrier may be smaller, reducing in size, or absent from subsequent aligners in the series.

The location and thickness of the barrier portion can be important. The greater the amount of surface area engagement of the aligner with the teeth, the more effective the tooth movement. Thus, it can be undesirable for the barrier portion to prevent or reduce the aligner's interaction with the teeth. A possible solution for this problem is to form the barrier portion as thinly as possible so that the base of the barrier covers as much of the dentition as possible. To ensure structural integrity of the barrier despite its thinness, the aligner can be fabricated from a refractory reference mold which contains structural support tabs that break away from the mold when the aligner is separated from the mold during the fabrication process. In other words, the tabs built into the mold via 3-D printing, stereolithography, or milling, separate from the mold and become embedded inside the aligner barrier portion in order to confer extra structural support to the aligner barrier feature. These embedded features are not limited to plastic materials, but can include metals, carbon fiber, and/or ceramics, given that many different types of materials besides plastic can now be 3-D printed as the refractory mold. Thus, in any of the devices described herein, the barrier may include a reinforcing support within the barrier, and this reinforcing support may be formed by support features that break away from the reference mold to become embedded inside the aligner barrier feature during the manufacturing process.

While many of the embodiments described herein have been applied to cases of anterior open bite, the same principles also apply to lateral open bite. The barrier portions could be applied to posterior regions of the aligner in such cases, either unilaterally or bilaterally. Furthermore, in some embodiments, the aligner and barrier portions can be used as standalone therapy for speech impediments, and not just for orthodontic treatments, as some patients may have trouble forming a proper seal with their mouth while speaking, even without an orthodontic appliance in place.

Figure 14:
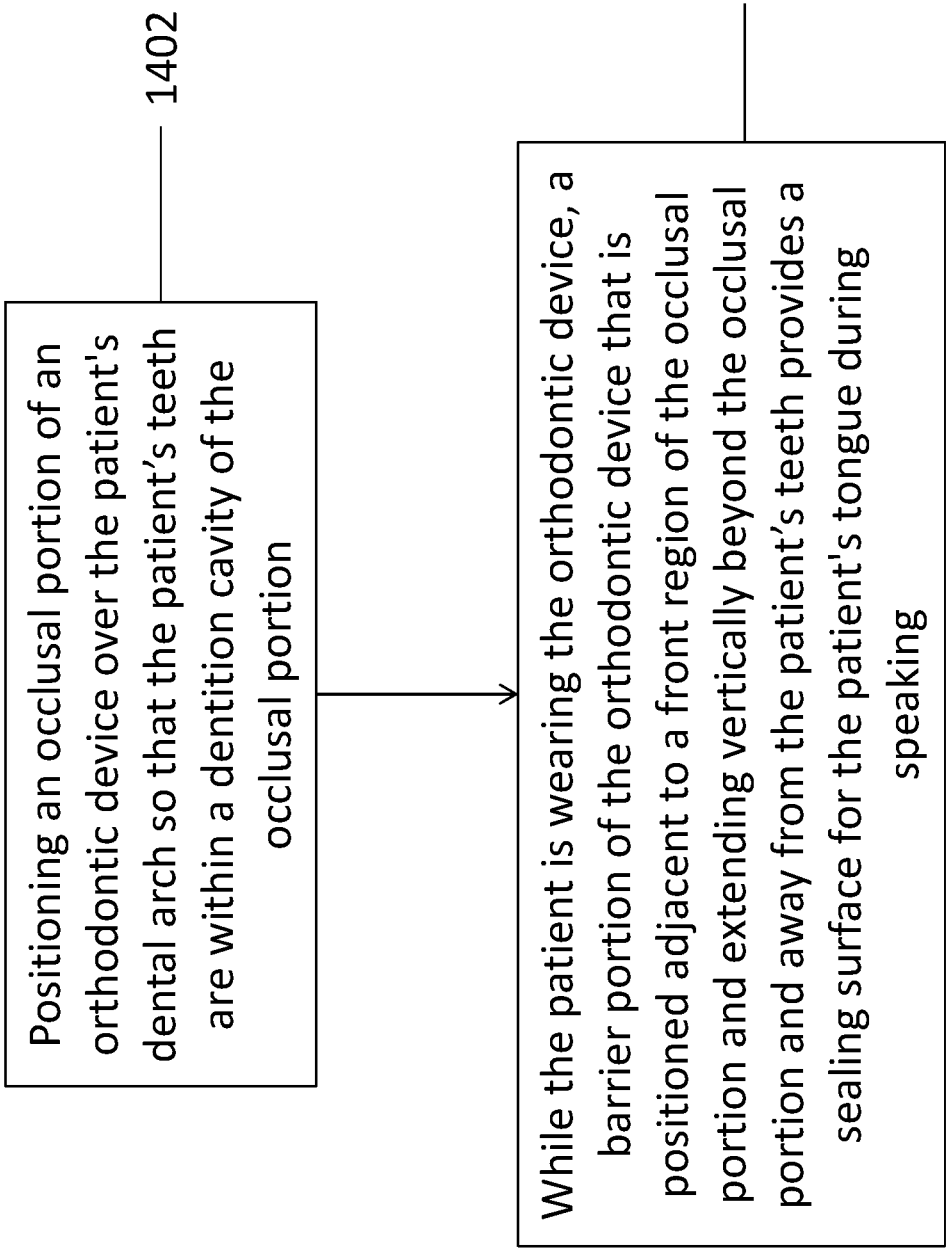
FIG. 14 illustrates an embodiment of a method of orthodontic treatment.

FIG. 14 shows an embodiment of a method of orthodontic treatment using devices such as those disclosed herein. As shown at block 1402, the method comprises positioning an occlusal portion of an orthodontic device over the patient's dental arch so that the patient's teeth are within a dentition-receiving cavity of the occlusal portion. As shown at block 1404, while the patient is wearing the orthodontic device, a barrier portion of the orthodontic device that is positioned adjacent to a region of the occlusal portion and extending vertically beyond the occlusal portion and away from the patient's teeth provides a sealing surface for the patient's tongue during speaking.

Figure 15:
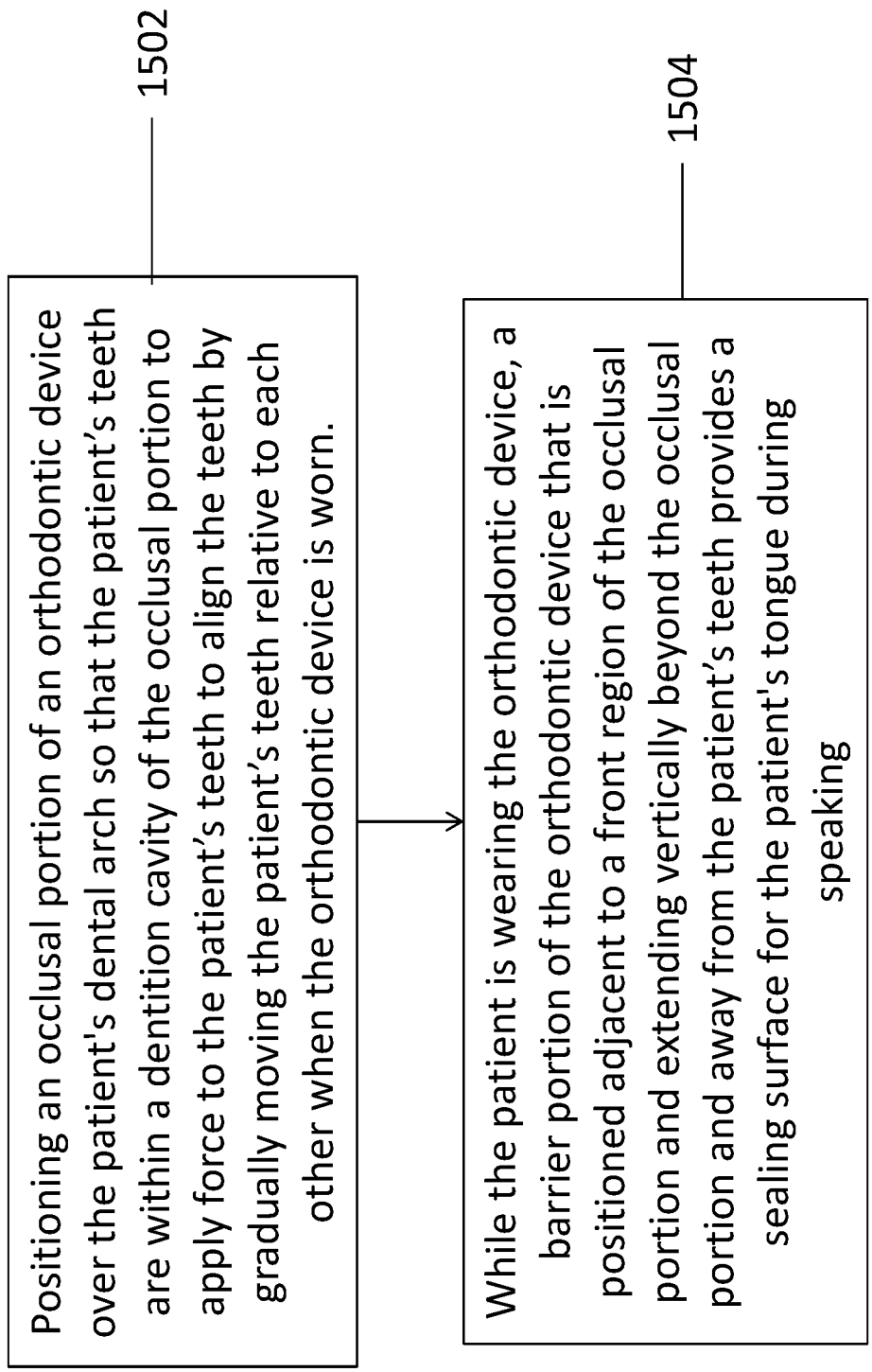
FIG. 15 illustrates another embodiment of a method of orthodontic treatment.

FIG. 15 depicts another embodiment of a method of orthodontic treatment using devices such as those disclosed herein. As shown at block 1502, the method comprises positioning an occlusal portion of an orthodontic device over the patient's dental arch so that the patient's teeth are within a dentition-receiving cavity of the occlusal portion to apply force to the patient's teeth to align the teeth by gradually moving the patient's teeth relative to each other when the orthodontic device is worn. As shown at block 1504, while the patient is wearing the orthodontic device, a barrier portion of the orthodontic device that is positioned adjacent to a region of the occlusal portion and extending vertically beyond the occlusal portion and away from the patient's teeth provides a sealing surface for the patient's tongue during speaking.

Figure 16:
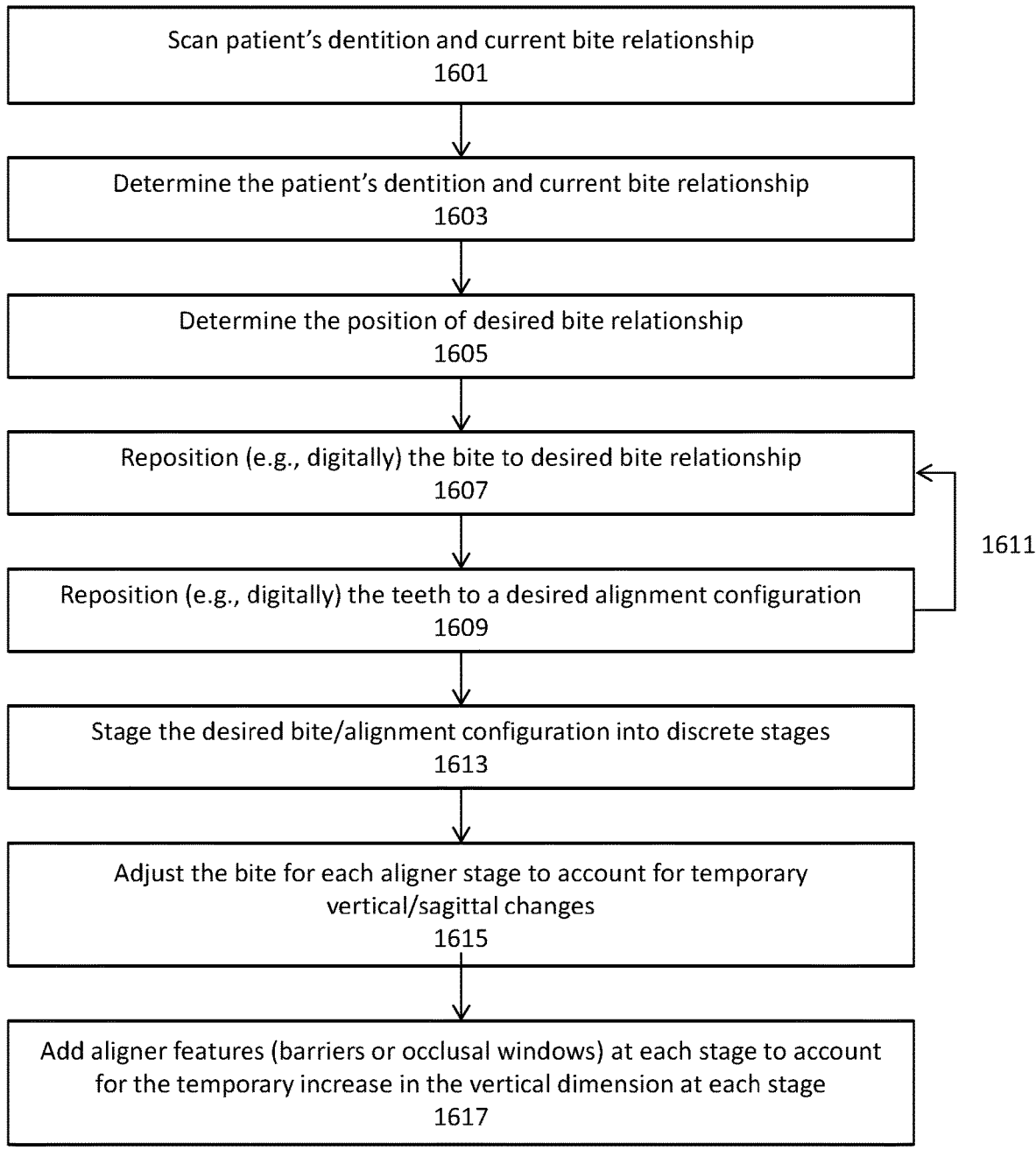
FIG. 16 illustrates a method for determining dimensions of a barrier portion of an orthodontic device as described herein.

Also described herein are methods of determining the dimensions of the barrier portion included as part of an aligner apparatuses described herein (or as part of an apparatus that is not configured to align the teeth). FIG. 16 is a schematic flow diagram illustrating a method of determining the dimensions of a barrier in an aligner apparatus. This method may be modified as necessary to determine the dimensions of a barrier for a device that is not also configured as an aligner, by omitting those steps not necessary to re-align the teeth. The models of the patient's dentition (including dimensions) may be made manually and/or electronically. For example, as shown in FIG. 16, the patient's dentition may be initially scanned 1601 or otherwise determined (e.g., using dental impressions, photographic or radiographic images, models, direct measurements, etc.). The patient's dentition may be scanned to determine the patient's dentition and current bite relationship 1603, or the bite relationship (e.g., between the teeth of the upper and lower jaws) may be otherwise determined. Next, the position of desired bite relationship is determined (e.g., Class 1 molar and canine relationship). This may be determined by scanning (e.g., the patient's mouth or a model of the dentition) the position of the desired bite relationship. For example, in a Class 2 patient, the lower jaw can be protruded and the teeth scanned in the "protruded" Class 1 bite relationship. In another example, in a Class 3 patient, physical models of the arches can be repositioned into a Class 1 relationship and the model relationship digitally captured. As an alternative to capturing altered physical bite relationships, the target bite may also be determined by digitally manipulating a digital representation of the patient's arches into the desired bite relationship. The goal in all of these manipulations is to create a model of the bite in a desired bite relationship 1607. Next, the teeth in the models of the arches may be repositioned to determine a desired relationship goal 1609. For example, the teeth may be digitally repositioned to determine a desired alignment configuration. These steps (1607, 1609) may be repeated 1611 until a desired setup of bite relationship/teeth alignment combination is achieved.

The desired movements of the teeth and/or changes in the bite from initial to goal may then be staged in discrete steps or stages, each step/stage representing an individual set of upper and lower aligners 1613. Thereafter, the bite position can be adjusted (e.g., digitally) for each aligner stage to account for temporary vertical/sagittal changes due to the repositioned teeth/bite, aligner thickness, bite repositioning aligner features, anterior bite ramp features, bite blocks, etc. 1615. Thereafter, aligner features (such as barriers or occlusal windows) may be added (e.g., digitally) at each stage to account for the temporary increase in the vertical dimension at each stage due to the aligner thickness and/or additional aligner features present 1617. Each aligner designed in this manner may then be manufactured (e.g., as described herein) and provided to the patient for treatment.

Figure 18:
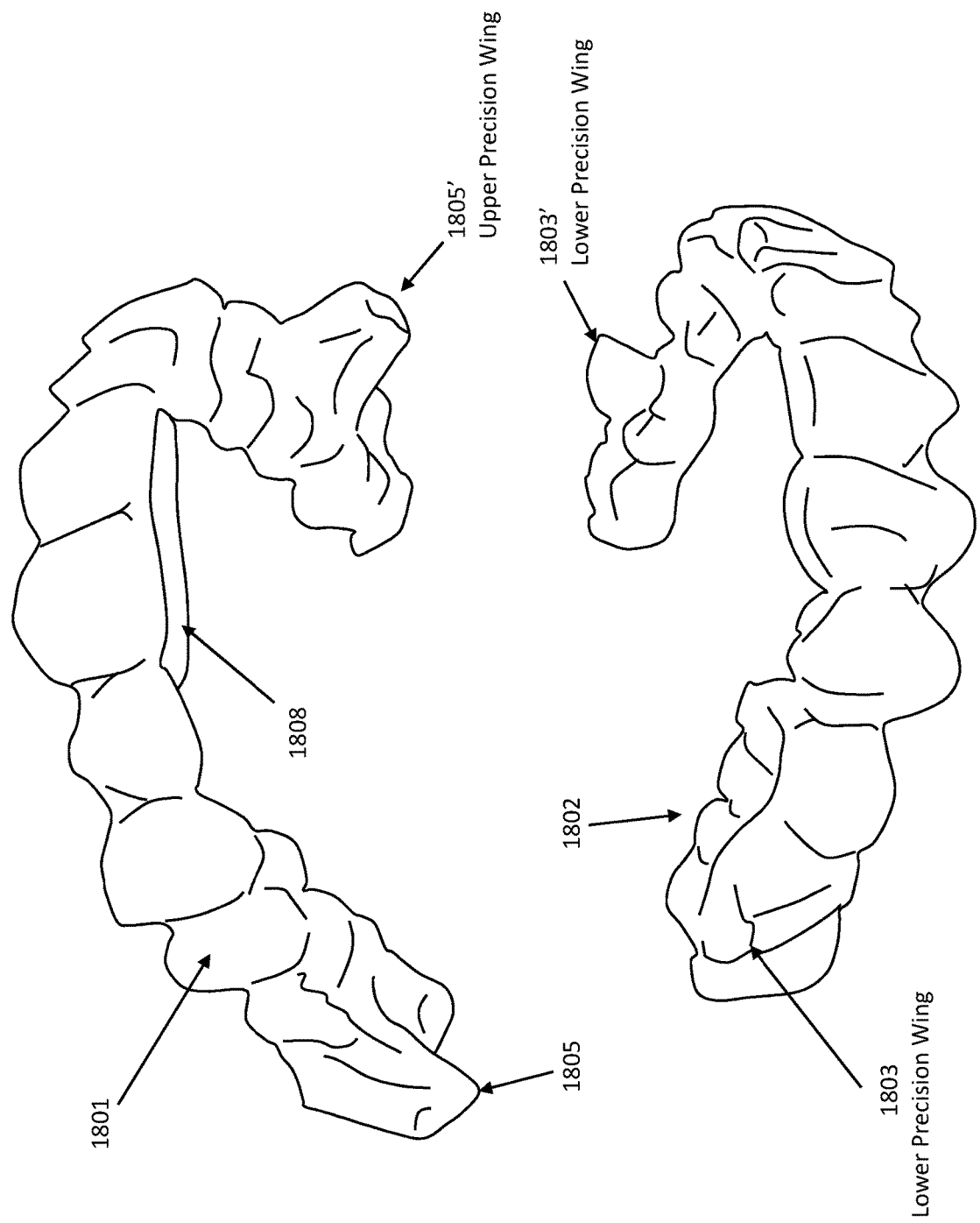
FIG. 18 illustrates another example of an orthodontic appliance including a barrier portion to enhance speech and/or patient comfort.

FIG. 18 is another example of an apparatus including a barrier portion extending laterally and adjacent to an occlusal portion. In this example the apparatus includes an upper appliance 1801 (upper arch appliance) and a lower appliance 1802 (lower arch appliance) that are configured to be worn over the patient's upper and lower arch, respectively. The upper and lower appliances in this example are configured as a mandibular advancement apparatus, in which each of the upper and lower appliances include wings that may engage with each other to drive the lower jaw forward during treatment when worn. For example, the upper arch appliance 1801 includes a first upper precision wing 1805' on a left sides and a second upper precision wing 1805 on the right side. The lower arch appliance may include a pair of wings (e.g., lower precision wings 1803, 1803') that may engage with each other to advance the patient's mandible. In FIG. 18, the upper arch appliance also includes a barrier 1808 (barrier portion). Alternatively or additionally, the lower arch appliance may include a barrier. In this example, the appliance(s) are formed as shell appliances that may also be configured to apply force to move the teeth. In some variation, the appliances are not configured to move individual teeth, but may be configured for mandibular advancement. When a patient is wearing the apparatus of FIG. 18, the upper and lower appliances may be worn together, so that when the patient's mouth is closed, the upper appliance may engage with the lower appliance, driving the lower appliance forward to advance the mandible; a seal may be formed between the patient's tongue and the barrier 1808, as air may be prevented from passing through the region. As described above, this may enhance comfort and may also prevent lisping or other speech difficulties.

In any of the appliance variations in which bite correction features are included (e.g., bite ramps, wings, etc.), the appliance(s) may include any of the features described herein, such as barriers and/or thinned or removed peak occlusal surface portions. In particular, any treatment and/or apparatus that tends to open the bite may benefit from an anterior compensation for speech enhancement as described herein, in order to avoid lisping in the patient. For example, appliances including a bite ramp, and/or variable thickness appliance, such as aligners.

Figure 19A:
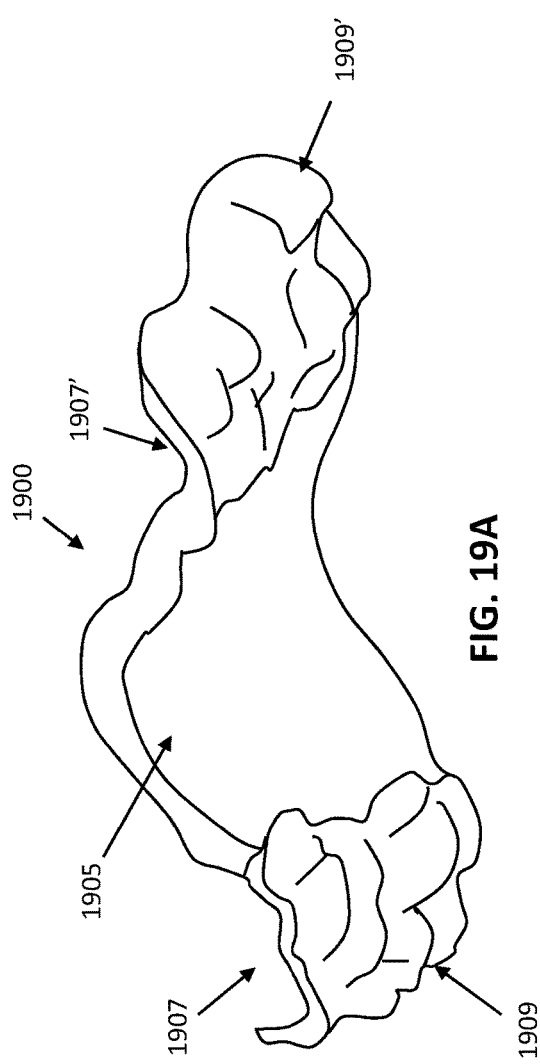
FIGS. 19A-19B illustrates an example of another orthodontic appliance that may be configured to include (as shown in FIG. 19B) a barrier portion to enhance speech and/or patient comfort.

Another example of an apparatus that may be configured to enhance speech (e.g., preventing lisping, etc.) is shown in FIG. 19A. FIG. 19A shows one in a series of palatal expanders 1900 that may be worn by a subject to expand the subject's palate (e.g., by widening the suture). Although any appropriate palatal expander may be used (including adjustable/expandable variations) the apparatus shown in FIG. 19A may be worn as part of a series of palatal expanders worn sequentially to adjust the width of the palate.

Figure 19B:
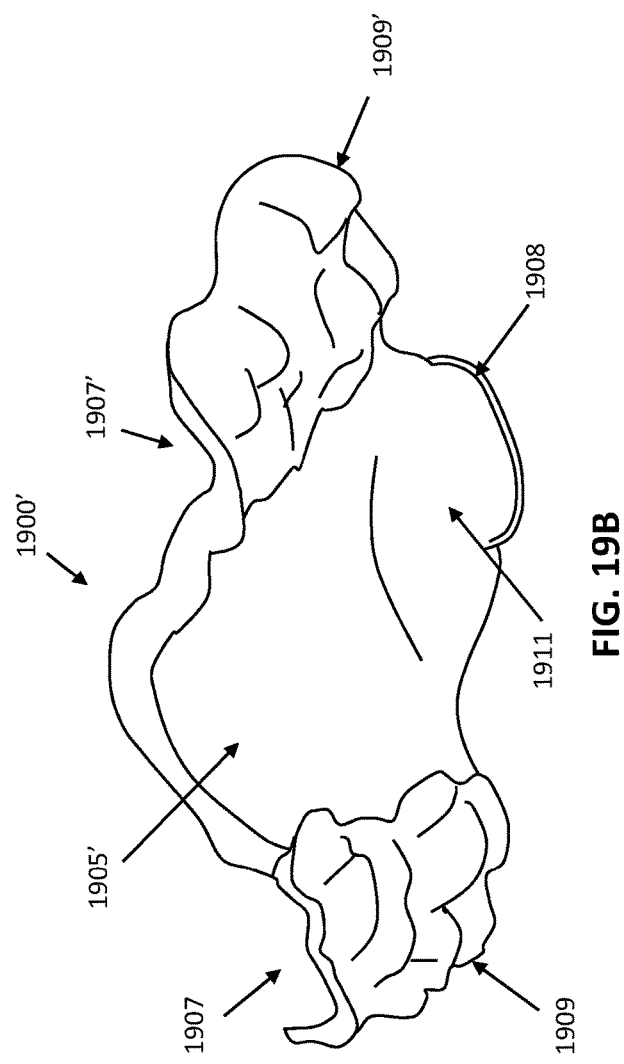

FIG. 19B shows a variations of the palatal expander of FIG. 19A with a barrier region 1908 at the anterior (front) end of the apparatus. In general, the palatal expander includes an occlusal portion having a dentition-receiving cavity 1907, 1907' extending laterally in an arch and having a first vertical height. In FIGS. 19A and 19B, the occlusal portion includes two dentition-receiving cavities, holding the molar and premolars; a palatal region 1905 extends lateral to the occlusal portion, e.g., between the first and second dentition-receiving cavities 1907, 1097'. Each dentition-receiving cavity is configured to fit over a portion of the patient's dental arch (e.g., the pre-molar and molars), and the dentition-receiving cavity may include an occlusal surface section adapted to be positioned over an occlusal surface of the patient's teeth. In FIG. 19B, the apparatus includes a barrier region 1908 that extends anteriorly from the palatal region on an extension or neck region 1911. The barrier portion therefore also extends laterally and adjacent to the occlusal portion, as descried above. The barrier portion may have a vertical height that is approximately the same height or a greater height than the maximum vertical height of the outer occlusal surface of the apparatus. As in any of these variations, the barrier portion may be laterally continuous to reduce or prevent air leakage, so that a patient's tongue may form a seal against the barrier portion when the patient is speaking while wearing the device.

Any of these apparatuses described herein may be used when the molars/premolars have a reduced height. For example, in some patients having bruxism (e.g., due to grinding of teeth), wearing down of the rear teeth, the jaw may overclose, resulting in a deep bite that may also lead to wear of the front teeth. Appliances to address this, including via restorative dentistry and/or the use of appliances (e.g., a series of aligners) to adjust the teeth, including straightening them, prior to placing restorative crowns on the teeth. Any of these appliances may include the structures, and particularly an anterior barrier structure, to enhance speech. Any of the methods, systems and/or components described herein (including U.S. Pat. No. 8,936,463, showing aligners with images of the target alignment shown on them). The methods and apparatuses described herein may prevent or limit leakage, including buccal leakage, through the apparatus.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that, the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value range of values), +1-10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An orthodontic device to manage speech articulation of a patient, the orthodontic device comprising:
   an occlusal portion having a dentition-receiving cavity configured to receive the patient's teeth and to exert repositioning forces on the patient's teeth, the occlusal portion having an incisor region configured to receive the patient's incisors, wherein the occlusal portion has a first vertical height; and
   a barrier portion extending laterally and adjacent to the occlusal portion, wherein the barrier portion is positioned lingual to the incisor region of the occlusal portion while the orthodontic device is worn by the patient, wherein the barrier portion has a second vertical height that is greater than the first vertical height, wherein the barrier portion comprises a sealing surface that is laterally continuous at least along a lateral length of the incisor region to reduce or prevent air leakage and form a seal against the patient's tongue, wherein the sealing surface is configured to preventing lisping while the patient is speaking and wearing the orthodontic device in the patient's mouth; and wherein a lingual side of the incisor region is physically separated from the barrier portion by a space to reduce pushing forces applied to the patient's incisors from the patient's tongue.

2. The orthodontic device of claim 1, wherein the barrier portion comprises a ridge.

3. The orthodontic device of claim 1, wherein the barrier portion comprises micro-perforations to allow local circulation of saliva or air.

4. The orthodontic device of claim 1, wherein the second vertical height of the barrier portion is more than about 1 mm higher than the first vertical height of the occlusal portion.

5. The orthodontic device of claim 1, wherein the second vertical height of the barrier portion is between about 2-4 mm higher than the first vertical height of the occlusal portion.

6. The orthodontic device of claim 1, wherein the barrier portion is positioned on a buccal side of the occlusal portion.

7. The orthodontic device of claim 1, further comprising one or more wings extending from the orthodontic device adjacent to the occlusal portion configured to engage with one or more wings extending from a second device worn on an opposite arch.

8. The orthodontic device of claim 1, further comprising a palatal region extending from the occlusal portion that is configured to be positioned adjacent to the patient's palate while the patient is wearing the orthodontic device.

9. The orthodontic device of claim 1, further comprising one or more bite ramps on the occlusal portion.

10. The orthodontic device of claim 1, wherein the dentition-receiving cavity is configured to fit over an upper dental arch of the patient.

11. The orthodontic device of claim 1, wherein the dentition-receiving cavity is configured to fit over a lower dental arch of the patient.

12. The orthodontic device of claim 1, wherein the barrier portion is formed integrally with the occlusal portion.

13. The orthodontic device of claim 1, wherein the barrier portion is formed separately from and is attached to the occlusal portion.

14. The orthodontic device of claim 1, wherein the barrier portion is tapered.

15. The orthodontic device of claim 1, wherein the occlusal portion is an upper occlusal portion adapted to fit over an upper dental arch of the patient, wherein the barrier portion is an upper barrier portion coupled to the upper occlusal portion, wherein the orthodontic device further comprises:
a lower occlusal portion adapted to fit over a lower dental arch of the patient, the lower occlusal portion including a lower barrier portion coupled to the lower occlusal portion, wherein one of the upper and lower barrier portions is positioned lingually relative to the other one of the upper and lower barrier portions.

16. The orthodontic device of claim 1, wherein the occlusal portion further includes a first canine region configured to receive a first canine of the patient and a second canine region configured to receive a second canine of the patient, wherein the barrier portion extends laterally from the first canine region to the second canine region of the occlusal portion.

17. The orthodontic device of claim 1, wherein the occlusal portion further includes a first premolar region configured to receive a first premolar of the patient and a second premolar region configured to receive a second premolar of the patient, wherein the barrier portion extends laterally from the first premolar region to the second premolar region of the occlusal portion.

\* \* \* \* \*